United States Patent
Lipsey et al.

(10) Patent No.: US 10,034,780 B2
(45) Date of Patent: *Jul. 31, 2018

(54) MODULAR AND LIGHTWEIGHT MYOELECTRIC PROSTHESIS COMPONENTS AND RELATED METHODS

(71) Applicant: REHABILITATION INSTITUTE OF CHICAGO, Chicago, IL (US)

(72) Inventors: James Lipsey, Oak Park, IL (US); Jon Sensinger, Fredericton (CA)

(73) Assignee: Rehabilitation Institute of Chicago, Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/614,187

(22) Filed: Feb. 4, 2015

(65) Prior Publication Data
US 2015/0216681 A1 Aug. 6, 2015

Related U.S. Application Data

(60) Provisional application No. 61/935,836, filed on Feb. 4, 2014.

(51) Int. Cl.
*A61F 2/58* (2006.01)
*A61F 2/72* (2006.01)
(Continued)

(52) U.S. Cl.
CPC .............. *A61F 2/582* (2013.01); *A61F 2/583* (2013.01); *A61F 2/585* (2013.01); *A61F 2/586* (2013.01);
(Continued)

(58) Field of Classification Search
CPC .......... A61F 2/583; A61F 2/585; A61F 2/586; A61F 2002/6836; A61F 2002/6845; A61F 2/58
See application file for complete search history.

(56) References Cited

U.S. PATENT DOCUMENTS 3,883,900 A * 5/1975 Jerard ..................... A61F 2/58
623/25
7,867,287 B2 1/2011 Puchhammer
(Continued)

FOREIGN PATENT DOCUMENTS

EP 1617103 A1 1/2006
EP 2532927 A2 12/2012
(Continued)

OTHER PUBLICATIONS

Dechev, N., et al., "Multiple finger, passive adaptive grasp prosthetic hand", Mechanism and Machine Theory, Oct. 1, 2001, 36(10):1157-1173.
(Continued)

*Primary Examiner* — Bruce E Snow
(74) *Attorney, Agent, or Firm* — Drinker Biddle & Reath LLP

(57) ABSTRACT

Prosthetic devices and, more particularly, modular myoelectric prosthesis components and related methods, are described. In one embodiment, a hand for a prosthetic limb may comprise a rotor-motor; a transmission, comprising a differential roller screw; a linkage coupled to the transmission; and at least one finger coupled to the linkage. In one embodiment, a component part of a wrist of a prosthetic limb may comprise an exterior-rotor motor, a planetary gear transmission, a clutch, and a cycloid transmission. In one embodiment, an elbow for a prosthetic limb may comprise an exterior-rotor motor, and a transmission comprising a planetary gear transmission, a non-backdrivable clutch, and a screw.

24 Claims, 14 Drawing Sheets

(51) Int. Cl.

| | |
|---|---|
| F16D 15/00 | (2006.01) |
| F16H 37/04 | (2006.01) |
| H02K 7/116 | (2006.01) |
| H02K 7/14 | (2006.01) |
| A61F 2/68 | (2006.01) |
| B25J 15/00 | (2006.01) |
| B25J 17/02 | (2006.01) |
| B25J 15/08 | (2006.01) |
| A61F 2/50 | (2006.01) |
| A61F 2/54 | (2006.01) |
| F16H 25/22 | (2006.01) |
| F16H 35/00 | (2006.01) |
| A61F 2/70 | (2006.01) |

(52) U.S. Cl.
CPC .............. *A61F 2/68* (2013.01); *A61F 2/72* (2013.01); *F16D 15/00* (2013.01); *F16H 37/041* (2013.01); *H02K 7/116* (2013.01); *H02K 7/14* (2013.01); *A61F 2002/5043* (2013.01); *A61F 2002/5072* (2013.01); *A61F 2002/543* (2013.01); *A61F 2002/587* (2013.01); *A61F 2002/6836* (2013.01); *A61F 2002/6845* (2013.01); *A61F 2002/6872* (2013.01); *A61F 2002/701* (2013.01); *A61F 2002/704* (2013.01); *A61F 2310/00047* (2013.01); *B25J 15/0009* (2013.01); *B25J 15/086* (2013.01); *B25J 17/0258* (2013.01); *F16H 25/2252* (2013.01); *F16H 2035/005* (2013.01)

(56) References Cited

U.S. PATENT DOCUMENTS

| | | | | |
|---|---|---|---|---|
| 8,016,893 | B2 * | 9/2011 | Weinberg | ............... B25J 9/102 475/149 |
| 8,100,986 | B2 | 1/2012 | Puchhammer et al. | |
| 8,257,446 | B2 | 9/2012 | Puchhammer | |
| 8,579,991 | B2 | 11/2013 | Puchhammer | |
| 8,663,339 | B2 | 3/2014 | Inschlag et al. | |
| 8,690,963 | B2 | 4/2014 | Puchhammer | |
| 2004/0181289 | A1 | 9/2004 | Bedard et al. | |
| 2008/0262634 | A1 | 10/2008 | Puchhammer | |
| 2011/0237381 | A1 | 9/2011 | Puchhammer | |
| 2011/0265597 | A1 | 11/2011 | Long | |
| 2012/0204665 | A1 | 8/2012 | Baudasse | |
| 2012/0286629 | A1 * | 11/2012 | Johnson | .................. B25J 9/08 310/68 B |

FOREIGN PATENT DOCUMENTS

| | | |
|---|---|---|
| EP | 2612619 A1 | 7/2013 |
| WO | 2008/092695 A1 | 8/2008 |
| WO | 2009/011682 A1 | 1/2009 |
| WO | 2010/018358 A2 | 2/2010 |
| WO | 2011/088964 A1 | 7/2011 |
| WO | 2011/143004 A2 | 11/2011 |

OTHER PUBLICATIONS

Sensinger, J., et al., "Exterior vs. Interior Rotors in Robotic Brushless Motors", 2011 IEEE International Conference on Robotics and Automation (ICRA), IEEE, May 9, 2011, pp. 2764-2770.

International Search Report and Written Opinion of the ISA/EP, issued in corresponding application PCT/US2015/014505, dated Apr. 21, 2015, 12 pages.

International Search Report and Written Opinion of the ISA/EP, issued in corresponding application PCT/US2015/014497, dated Jul. 24, 2015, 19 pages.

R. F. FF.Weir and J.W. Sensinger, "Design of artificial arms and hands for prosthetic applications," in Biomedical Engineering and Design Handbook, vol. 2, M. Kutz, Ed., 2nd ed. New York, NY, USA: McGraw-Hill, 2009, pp. 537-598.

D. Childress and R. F. FF. Weir, "Control of limb prostheses," in Atlas of Amputations and Limb Deficiencies, D. G. Smith, J. W. Michael, and J. H. Bowker, Eds., 3rd ed. Rosemont, IL, USA: American Academy of Orthopaedic Surgeons, 2004.

A. Fougner, O. Stavdahl, P. J. Kyberd, Y. G. Losier, and P. A. Parker, "Control of upper limb prostheses: Terminology and proportional myoelectric control—A review," IEEE Trans. Neural Syst. Rehabil. Eng.,vol. 20, No. 5, pp. 663-677, Sep. 2012.

E. Scheme and K. Englehart, "Electromyogram pattern recognition for control of powered upper-limb prostheses: State of the art and challenges for clinical use," J. Rehabil. Res. Dev., vol. 48, No. 6, pp. 643-659, 2011.

C. Cipriani et al., "On the shared control of an EMG-controlled prosthetic hand: Analysis of user—prosthesis interaction," IEEE Trans. Robot., vol. 24, No. 1, pp. 170-184, Feb. 2008.

T. A. Kuiken et al., "Targeted muscle reinnervation for real-time myoelectric control of multifunction artificial arms.," JAMA, vol. 301, No. 6, pp. 619-628, 2009.

E. A. Biddiss and T. T. Chau, "Upper limb prosthesis use and abandonment: A survey of the last 25 years," Prosthetics Orthotics Int., vol. 31, No. 3, pp. 236-257, 2007.

M. S. Pinzur, J. Angelats, T.R. Light,R. Izuierdo, and T. Pluth, "Functional outcome following traumatic upper limb amputation and prosthetic limb fitting," J. Hand Surgery, Amer. Vol., vol. 19, pp. 836-839, 1994.

L. Resnik, S. L. Klinger, and K. Etter, "The DEKA arm: Its features, functionality, and evolution during the veterans affairs study to optimize the DEKA arm," Prosthetics Orthotics Int., vol. 38, pp. 492-504, 2014.

J. T. Belter, J. L. Segil, A. M. Dollar, and R. F. Weir, "Mechanical design and performance specifications of anthropomorphic prosthetic hands: A review.," J. Rehabil. Res. Dev., vol. 50, No. 5, pp. 599-618, Jan. 2013.

N.Wettels, A. R. Parnandi, G. E. Loeb, and G. S. Sukhatme, "Grip control using biomimetic tactile sensing systems," IEEE/ASME Trans. Mechatronics, vol. 14, No. 6, pp. 718-723, Dec. 2009.

E. D. Engeberg and S. G. Meek, "Adaptive sliding mode control for prosthetic hands to simultaneously prevent slip and minimize deformation of grasped objects," IEEE/ASME Trans. Mechatronics, vol. 18, No. 1, pp. 376-385, Feb. 2013.

D. D. Damian, T. H. Newton, R. Pfeifer, and A. M. Okamura, "Artificial tactile sensing of position and slip speed by exploiting geometrical features," IEEE Trans. Mechatronics, vol. 20, No. 1, pp. 263-274, Feb. 2015.

M. S. Johannes, J. D. Bigelow, J. M. Burck, S. D. Harshbarger, and M. V Kozlowski, "An overview of the developmental process for the modular prosthetic limb," John Hopkins APL Tech.Dig., vol. 30, No. 3, pp. 207-216, 2011.

E. Biddiss and T. Chau, "Upper-limb prosthetics: Critical factors in device abandonment.," Amer. J. Phys. Med. Rehabil., vol. 86, No. 12, pp. 977-987, Dec. 2007.

E. Biddiss, D. Beaton, and T. Chau, "Consumer design priorities for upper limb prosthetics," Disabil. Rehabil. Assist. Technol., vol. 2, No. 6, pp. 346-357, Jan. 2007.

J. W. Sensinger, "Selecting motors for robots using biomimetic trajectories:Optimum benchmarks, windings, and other considerations," in Proc. IEEE Conf. Robot. Autom., Anchorage, AL, USA, 2010, pp. 4175-4181.

J. W. Sensinger, S. D. Clark, and J. F. Schorsch, "Exterior vs. interior rotors in robotic brushless motors," in Proc. IEEE Conf. Robot. Autom., Shanghai, China, 2011, pp. 2764-2770.

J. Choi et al., "Design of high power permanent magnet motor with segment rectangular copperwire and closed slot opening on electric vehicles," IEEE Trans. Magn., vol. 46, No. 9, pp. 3701-3704, Jun. 2010.

J.W. Sensinger, "Efficiency of high-sensitivity gear trains, such as cycloid drives," J. Mech. Des., vol. 135, No. 7, p. 71006, 2013.

(56) References Cited

OTHER PUBLICATIONS

J. W. Sensinger and J. H. Lipsey, "Cycloid vs. harmonic drives for use in high ratio, single stage robotic transmissions," presented at the IEEE Conf. Robot. Autom., St. Paul, MN, USA, 2012.
J. W. Sensinger and R. E. F. Weir, "User-modulated impedance control of a prosthetic elbow in unconstrained, perturbed motion," IEEE Trans. Biomed. Eng., vol. 55, No. 3, pp. 1043-1055, Mar. 2008.
T. Morita and S. Sugano, "Development of 4-D.O.F. manipulator using mechanical impedance adjuster," in Proc. IEEE Int. Conf. Robot. Autom., 1996, pp. 2902-2907.
A. Albu-Schaffer, O. Eiberger, M. Grebenstein, S. Haddadin, C. Ott, T. Wimbock, S.Wolf, and G. Hirzinger, "Soft robotics," IEEE Robot. Autom. Mag., vol. 15, No. 3, pp. 20-30, 2008.
J. W. Sensinger, "Unified approach to cycloid drive profile, stress, and efficiency optimization," ASME J. Mech. Des., vol. 132, No. 2, pp. 1-5, 2010.
C.-F. Hsieh, "Dynamics analysis of cycloidal speed reducers with pinwheel and nonpinwheel designs," ASME J. Mech. Des., vol. 136, No. 9, p. 091008, Jun. 2014.
M. Controzzi, C. Cipriani, and M. C. Carrozza, "Miniaturized nonback-drivable mechanism for robotic applications," Mech. Mach. Theory, vol. 45, No. 10, pp. 1395-1406, Oct. 2010.
F. Montagnani,M. Controzzi, and C. Cipriani, "Is it finger or wrist dexterity that is missing in current hand prostheses?" IEEE Trans. Neural Syst. Rehabil. Eng., vol. 23, No. 4, pp. 600-609, Jul. 2015.
C. Light, P. H. Chappell, and P. J. Kyberd, "Establishing a standardized clinical assessment tool of pathologic and prosthetic hand function: Normative data, reliability, and validity," Arch. Phys. Med. Rehabil., vol. 83, pp. 776-783, 2002.
M. L. Zampagni, D. Casino, S. Martelli, A. Visani, and M. Marcacci, "A protocol for clinical evaluation of the carrying angle of the elbow by anatomic landmarks," J. Shoulder Elbow Surg., vol. 17, No. 1, pp. 106-112, 2008.
J. B. Tang, "General concepts of wrist biomechanics and a view from other species," J. Hand Surg., Eur. Vol., vol. 33, No. 4, pp. 519-525, Aug. 2008.
Y. Hojjat and M. Mahdi Agheli, "A comprehensive study on capabilities and limitations of roller-screw with emphasis on slip tendency," Mech. Mach. Theory, vol. 44, No. 10, pp. 1887-1899, 2009.
Whiteside, Steven R et al. "Practice Analysis Task Force: Practice Analysis of the Disciplines of Orthotics and Prosthetics." American Board for Certification in Orthotics and Prosthetics, Inc, 1-51. 2000.
A. H. R. Bellman, T. Sugar, R. D. Bellman, M. A. Holgate, and T. G. Sugar, "SPARKy 3: Design of an active robotic ankle prosthesis with two actuated degrees of freedom using regenerative kinetics," in Proc. IEEE/RAS-EMBS Int. Conf. Biomed. Robot. Biomechatron., 2008, pp. 511-516.
L. G. Sutton, A. Clawson, T. W. Williams, J. H. Lipsey, and J. W. Sensinger, "Towards a universal coupler design for modern powered prostheses," presented at the Myoelect. Controls Symp., Fredericton, NB, Canada, 2011.
C. W. Heckathorne, "Components for electric-powered systems," in Atlas of Amputations and Limb Deficiencies, 3rd ed. Rosemont, IL, USA: American Academy of Orthopaedic Surgeons, 2004, pp. 145-172.

A. W. Wilson, Y. G. Losier, P. A. Parker, and D. F. Lovely, "A bus-based smart myoelectric electrode/amplifier-system requirements," IEEE Trans. Instrum. Meas., vol. 60, No. 10, pp. 3290-3299, Oct. 2011.
E. Scheme, B. Lock, L. Hargrove, W. Hill, U. Kuruganti, and K. Englehart, "Motion normalized proportional control for improved pattern recognition-based myoelectric control," IEEE Trans. Neural Syst. Rehabil. Eng., vol. 22, No. 1, pp. 149-157, Jan. 2014.
C. Toledo, A. Simon, R. Munoz, A. Vera, L. Leija, and L. Hargrove, "A comparison of direct and pattern recognition control for a two degree-of-freedom above elbow virtual prosthesis," in Proc. IEEE Annu. Int. Conf. Eng. Med. Biol. Soc., 2012, pp. 4332-4335.
C. L. Chicoine, A. M. Simon, and L. J. Hargrove, "Prosthesis-guided training of pattern recognition-controlled myoelectric prosthesis," in Proc. IEEE Annu. Int. Conf. Eng. Med. Biol. Soc., 2012, vol. 60611, pp. 1876-1879.
V. J. Majd and M. A. Simaan, "A continuous friction model for servo systems with stiction," in Proc. Int. Conf. Control Appl., 1995, pp. 296-301.
M. R. Kermani, R. V. Patel, and M. Moallem, "Friction identification and compensation in robotic manipulators," IEEE Trans. Instrum. Meas., vol. 56, No. 6, pp. 2346-2353, Dec. 2007.
A. Ninu, S. Dosen, S. Muceli, F. Rattay, H. Dietl, and D. Farina, "Closed-loop control of grasping with a myoelectric hand prosthesis: Which are the relevant feedback variables for force control?" IEEE Trans. Neural Syst. Rehabil. Eng., vol. 22, No. 5, pp. 1041-1052, Sep. 2014.
S. Raspopovic et al., "Restoring natural sensory feedback in real-time bidirectional hand prostheses," Sci. Transl. Med., vol. 6, No. 222, 2014.
B. A. Kent, N. Karnati, and E. D. Engeberg, "Electromyogram synergy control of a dexterous artificial hand to unscrew and screw objects," J. Neuroeng. Rehabil., vol. 11, No. 1, 2014.
W. J. Gaine, C. Smart, and M. Bransby-Zachary, "Upper limb traumatic amputees. Review of prosthetic use," J. Hand Surg. Amer., vol. 22 B, No. 1, pp. 73-76, 1997.
L. A. Miller and S. Swanson, "Summary and recommendations of the Academy's State of the Science conference on upper limb prosthetic outcome measures," J. Prosthetics Orthotics, vol. 21, pp. 83-89, 2009.
R. H. Jebsen, N. Taylor, R. B. Trieschmann, M. J. Trotter, and L. A. Howard, "An objective and standardized test of hand function," Arch. Phys. Med. Rehabil., vol. 50, No. 6, pp. 311-319, 1969.
J.W. Sensinger. "Unified Approach to Cycloid Drive Profile, Stress, and Efficiency Optimization," Journal of Mechanical Design, vol. 132, Feb. 2010, pp. 024503-1-024503-5. 2010.
D.W.Tan, M.A. Schiefer, M.W. Keith, J.R. Anderson, J. Tyler, D.J. Tyler, "A neural interface provides long-term stable natural touch perception," Science Translational Medicine, vol. 6, issue 257, Oct. 8, 2014, pp. 1-11.
Belter et al., "Mechanical design and performance specifications of anthropomorphic prosthetic hands: A review," URRD, vol. 50(5), 2013, pp. 599-618.
Maxon Precision Motors, Inc., "Maxon flat motor: EC 10 flat 10 mm, brushless, 0.2 Watt," Specification, May 2011, p. 181.
Maxon Precision Motors, Inc., "Maxon EC motor: EC 10 10 mm, brushless, 8 Watt," Specification, May 2011, p. 140.

* cited by examiner

MODULAR AND LIGHTWEIGHT MYOELECTRIC PROSTHESIS COMPONENTS AND RELATED METHODS

CROSS-REFERENCE TO RELATED APPLICATIONS

The present application claims priority to U.S. Provisional Patent Application 61/935,836, filed on Feb. 4, 2014, which is incorporated herein by reference in its entirety.

STATEMENT REGARDING FEDERALLY SPONSORED RESEARCH OR DEVELOPMENT

This invention was made with government support under W81XWH-11-1-0720 and W81XWH-10-2-0033 awarded by the United States Army. The government has certain rights in the invention.

TECHNICAL FIELD

The present disclosure is generally directed to prosthetic devices and, more particularly, to modular myoelectric prosthesis components and related methods.

BACKGROUND

Amputation of the arm causes significant disability, which is most effectively treated by replacement of the missing limb with a prosthetic device. Body-powered prostheses use a Bowden cable that couples motion of an intact joint to movement of the terminal device. Myoelectric prostheses control motorized joints via commands sent through the patients' residual muscles and sensed by surface electrodes embedded in the prosthetic socket.

Advances in embedded controllers, battery density, and motor design have increased the number of myoelectric prosthesis users. However, existing myoelectric prostheses are heavy, and wearing them constantly does not appeal to many amputees. Additionally, such prostheses are often too large for many amputees, such as children and many women. Several multi-function arms have recently come on the market, including Otto Bock's Michelangelo Hand, the Touch Bionics Hand, the BeBionics Hand, and the Vincent Hand. These devices are typically designed for a 50th percentile male (22.2 cm/8.75" hand circumference). Other hands are being developed in research, but use components that limit the strength, weight, and small volumes the limbs can achieve.

SUMMARY

In one embodiment, a hand for a prosthetic limb may comprise a rotor-motor; a transmission, comprising a differential roller screw; a linkage coupled to the transmission; at least one finger coupled to the linkage; wherein the rotor-motor is configured to actuate the transmission, the transmission is configured to actuate the linkage, and the linkage is configured to flex or extend the at least one finger. At least one finger of the hand may comprise an index finger and middle finger. The index finger and the middle finger may be fused. At least one finger may comprise an independently hinged finger, such as a ring finger or a pinky finger. The hand may comprise a side bar coupled to the transmission for transmitting motion to at least one of the independently hinged fingers. The linkage of the hand may generate an anatomically natural motion. The hand may further comprise a controller for the control of the hand. The hand may comprise an exoskeleton, which may be made from aluminium. A portion of the exoskeleton may be attachable to a wrist flexor. The rotor-motor of the hand may be a brushless interior rotor motor. The transmission of the hand may further comprise a gear set comprising at least one gear, the gear set positioned between the rotor-motor and the differential roller screw, the gear set adapted to translate rotational motion from the rotor-motor into linear motion of the differential roller screw. The transmission may further comprise a non-backdrivable clutch. The clutch may comprise a cam comprising an annulus, an input side that is adapted to receive an input force, and an output side that is adapted to provide an output force; a pin and a roller, each located adjacent to the input side of the cam; wherein the cam is adapted so that movement of the cam in response to the input force causes the pin to push the roller out of contact with the annulus, when a force is applied to the input side of the cam, the pin pushes the roller out of contact with the annulus to allow for movement of the cam. The transmission may further comprise a gear set comprising at least one gear, the gear set positioned between the rotor-motor and the differential roller screw, the gear set adapted to translate rotational motion from the rotor-motor into linear motion of the differential roller screw. The hand may further comprising a casing for housing the differential roller screw. The cam may be positioned at the base of the hand, the casing may have a proximal end that is adjacent to the cam, and the casing may be positioned in the interior of the hand. The clutch may further comprise a mechanical fuse. The linkage of the hand may be coupled to the transmission via a pivot. The hand may further comprise a thumb comprising exactly one motor and a gear set comprising at least one gear, wherein the motor actuates only the thumb. The hand may be adapted to be positioned in more than one, or in all, of the following positions: relaxed, palm-flat, chuck grip, and cylindrical grip.

In one embodiment, a wrist for a prosthetic limb may comprise a wrist rotator comprising a first exterior-rotor motor, a first planetary gear transmission, a first clutch and a first cycloid transmission, in a transmission arrangement such that actuation of the first exterior-rotor motor causes movement through the first planetary gear transmission, first clutch, and first cycloid transmission to cause rotation of the wrist; and a wrist flexor comprising a second exterior-rotor motor, a second planetary gear transmission, a second clutch and a second cycloid transmission, in a transmission arrangement such that actuation of the second exterior-rotor motor causes movement through the second planetary gear transmission second first clutch, and second cycloid transmission to cause flexion of the wrist. The first clutch may comprise a non-backdrivable mechanism for preventing output motion of the first clutch to be transmitted to the first cycloid transmission. The second clutch may comprise a non-backdrivable mechanism for preventing output motion of the first clutch to be transmitted to the first cycloid transmission. At least one of the first planetary gear transmission and the second planetary gear transmission may be a single-stage planetary gear transmission. The torque ratio of the first planetary gear transmission may be about 3.71:1 and the torque ratio of the first cycloid transmission may be about 16:1. The wrist may comprise an interface on the wrist rotator for transmitting signals across an access of rotation of the wrist rotator. The interface may comprise an interface for power signals and an interface for ground signals. The interface may further comprise an interface for at least two communication signals. The wrist may comprise a mechanical stop to limit motion of the wrist flexor. The wrist rotator and the wrist flexor may be connected by a coupler that allows for the transmission of power from the wrist rotator to the wrist flexor. The wrist flexor may be set on a rotation axis skewed by between about 10 to 30 degrees to provide radial/ulnar deviation. The non-backdrivable mechanism may comprise a plurality of rollers and a plurality of springs.

In one embodiment, a component part of a wrist of a prosthetic limb may comprise an exterior-rotor motor, a planetary gear transmission, a clutch, and a cycloid transmission. The exterior-rotor motor, a planetary gear transmission, a clutch, and a cycloid transmission may be in a transmission arrangement such that actuation of the exterior-rotor motor causes movement through the planetary gear transmission, clutch, and cycloid transmission to cause movement of the wrist. The clutch may comprise a non-backdrivable mechanism for preventing output motion of the clutch to be transmitted to the cycloid transmission. The planetary gear transmission may be a single-stage planetary gear transmission. The movement of the wrist may be a rotational movement. The torque ratio of the planetary gear transmission may be about 3.71:1 and the torque ratio of the cycloid transmission may be about 16:1. The movement of the wrist may be a flexion movement. The wrist component may be set on a rotation axis skewed by between about 10 to 30 degrees to provide radial/ulnar deviation.

In one embodiment, an elbow for a prosthetic limb may comprise an exterior-rotor motor; and a transmission comprising a planetary gear transmission, a non-backdrivable clutch, and a screw. The screw may be adapted to receive a rotational force in a first direction from the clutch, and in response to the rotational force in the first direction, extend linearly with respect to the transmission so as to cause the elbow to flex. The clutch may comprise a cam comprising an annulus, an input side that is adapted to receive an input force, and an output side that is adapted to provide an output force; and a pin and a roller, each located adjacent to the input side of the cam. The cam may be adapted so that movement of the cam in response to the input force causes the pin to push the roller out of contact with the annulus, when a force is applied to the input side of the cam, the pin pushes the roller out of contact with the annulus to allow for movement of the cam. The elbow may comprise a frame adapted to surround the transmission and having an opening for receiving a battery; a socket connector coupled to the elbow, for attaching the elbow to a prosthetic socket; and a position sensor for indicating the rotational movement of the elbow. The screw may be further adapted to receive a rotational force in a second direction from the clutch, and in response to the rotational force in the second direction, retract linearly with respect to the transmission so as to cause the elbow to extend. The socket connector may be coupled to the elbow at a carrying angle. The screw may be a differential roller screw. The elbow may comprise a pivot for the flexion or extension of the elbow. The pivot may be encased in a bushing made of a nonlinear compliant material. The elbow may have a 135 degree range of motion between full flexion and full extension. The elbow may further comprise a shear pin. The elbow may further comprise a first limb portion and a second limb portion coupled together at an elbow joint. A first end of the screw may be coupled to the first limb portion at a bracket. The transmission may be coupled to the second limb portion at a transmission joint. When the screw extends and retracts linearly, the screw may pivot with respect to the bracket. The transmission may pivot with respect to the second limb portion.

In one embodiment, an elbow component for a prosthetic limb may comprise a first limb portion and a second limb portion coupled together at an elbow joint. The transmission may comprise a screw. A first end of the screw may be coupled to the first limb portion at a bracket. The transmission may be coupled to the second limb portion at a transmission joint. The screw and the hinge may be adapted so that when the screw extends linearly in a direction away from the transmission, the screw may apply a force on the bracket that causes the first limb portion to rotate about the elbow joint towards the second limb portion. The screw and the hinge may be adapted so that when the screw retracts linearly in a direction towards the transmission, the screw may apply a force on the bracket that causes the first limb portion to rotate about the elbow joint away from the second limb portion. The transmission and the elbow joint may be adapted so that when the screw extends linearly in a direction away from the transmission, the transmission may rotate about the transmission joint in a first direction. The transmission and the elbow joint may be adapted so that when the screw retracts linearly in a direction towards the transmission, the transmission may rotate about the transmission joint in a second direction opposite to the first direction. When the screw extends and retracts linearly, the screw may pivot with respect to the bracket and the transmission may pivot with respect to the second limb portion. The screw may extend and retract in response to actuation of the transmission. The elbow component may comprise a position sensor to indicate rotational movement of the elbow component. The elbow component may comprise a bushing made of a nonlinear compliant material that encases the transmission pivot; a socket connector coupled to either the first limb portion or the second limb portion; and a frame that surrounds the transmission and is adapted to receive a battery. The screw may be a differential roller screw. The socket connector may be coupled to the first limb portion at a carrying angle. The screw may be coupled to the bracket by a nut.

In one embodiment, a transmission for an elbow joint of a prosthetic limb may comprise a motor, a gear set comprising at least one gear, a non-backdrivable clutch, and a screw, adapted to be housed in a frame pivotally attached to a second portion of the limb. The screw may be adapted to be coupled to a first portion of the limb that is pivotable with respect to the second portion of the limb. The screw may be adapted to receive a rotational force in a first direction from the clutch, and in response to the rotational force in the first direction, extend linearly with respect to the transmission. The screw may be adapted to receive a rotational force in a second direction from the clutch, and in response to the rotational force in the second direction, retract linearly with respect to the transmission. The non-backdrivable clutch may comprise a cam comprising an annulus, an input side that is adapted to receive an input force, and an output side that is adapted to provide an output force; and a pin and a roller, each located adjacent to the input side of the cam. The cam may be adapted so that movement of the cam in response to the input force causes the pin to push the roller out of contact with the annulus, and when a force is applied to the input side of the cam, the pin pushes the roller out of contact with the annulus to allow for movement of the cam. The screw may be a differential roller screw.

The features described above are available in different embodiments of the prosthetic components described, and should not be interpreted to limit or narrow the scope of the claims. The features described herein may additionally be applied in different combinations in different embodiments.

DRAWINGS

While the appended claims set forth the features of the present techniques with particularity, these techniques may be best understood from the following detailed description taken in conjunction with the accompanying drawings of which:

DESCRIPTION

Figure 1:
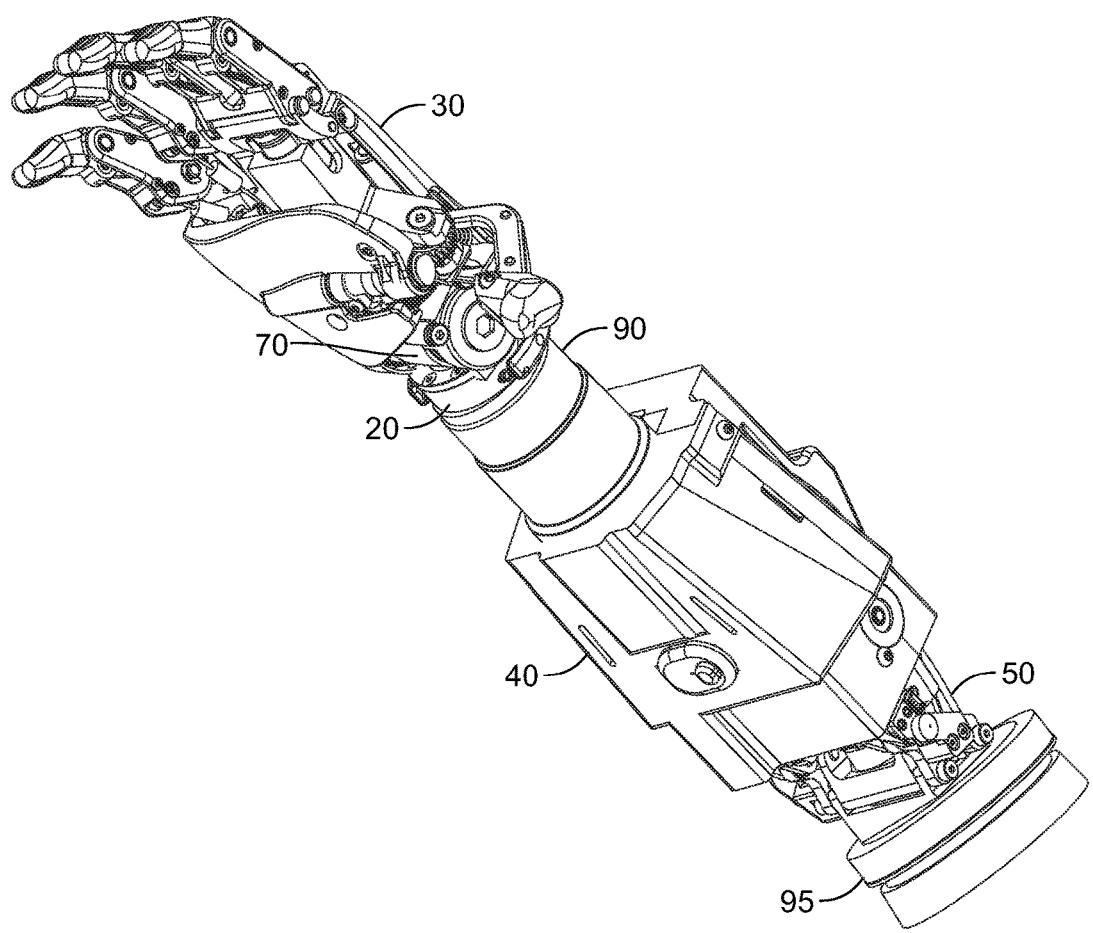
FIG. 1 is a lateral view of a prosthetic limb according to an embodiment.

Turning to the drawings, wherein like reference numerals refer to like elements, the following description is based on embodiments of the claims and should not be taken as limiting the claims with regard to alternative embodiments that are not explicitly described herein.

Embodiments described herein relate to a modular and lightweight prosthetic limb and its modular components. In one embodiment, the prosthetic limb delivers specified torques and motion profiles utilizing its small size, small mass, durable design, and specified axis rotations. The arm maintains different motion profiles, each of which may vary the position, speed, and/or acceleration of its various components. The limb is modular, allowing a user to either use all of the components described herein or swap them out for alternate parts. Different components of the limb may use exterior-rotator motors, which have their rotor on the outside of the stator, as described, for example, in Sensinger, Clark & Schorsch, "Exterior vs. Interior rotors in robotic brushless motors," in IEEE Conference on Robotics and Automation, Shanghai China, 2011, pp. 2764-2770.

FIG. 1 shows a lateral view of a prosthetic limb 10 ("limb 10"). The components of the limb 10 shown in FIG. 1 include a universal coupler 20, a hand 30, a forearm 150, an elbow 50, a wrist flexor 70, and a wrist rotator 90. The limb 10 further includes a socket connector 95 that connects to the distal end of a user's prosthetic socket (not shown). The hand 30, the wrist flexor 70, the wrist rotator 90, and the elbow 50 are modular, allowing clinicians to provide an amputee user with only the components he or she needs based on his or her level of amputation. For example, a below-elbow amputee, whose arm still has the elbow, would not need the elbow 50 component. Each modular component is connected by a CAN bus communication standard for prosthetic arms and a universal coupler 20, allowing users to swap different hands for different applications such as an electric hook, a lightweight hand, or a more powerful hand. The universal coupler 20 allows a user to attach, detach, spin, and lock in a component of the arm. One possible embodiment of the universal coupler 20 is described in Sutton, Clawson, et al, "Towards a universal coupler design for modern powered prostheses," Myoelectric Controls Symposium, Fredericton, Canada, 2011.

In one embodiment, the limb 10 may be covered by a cosmesis to provide protection from liquids and dirt, and to result in appearing as a natural limb.

Figure 3:
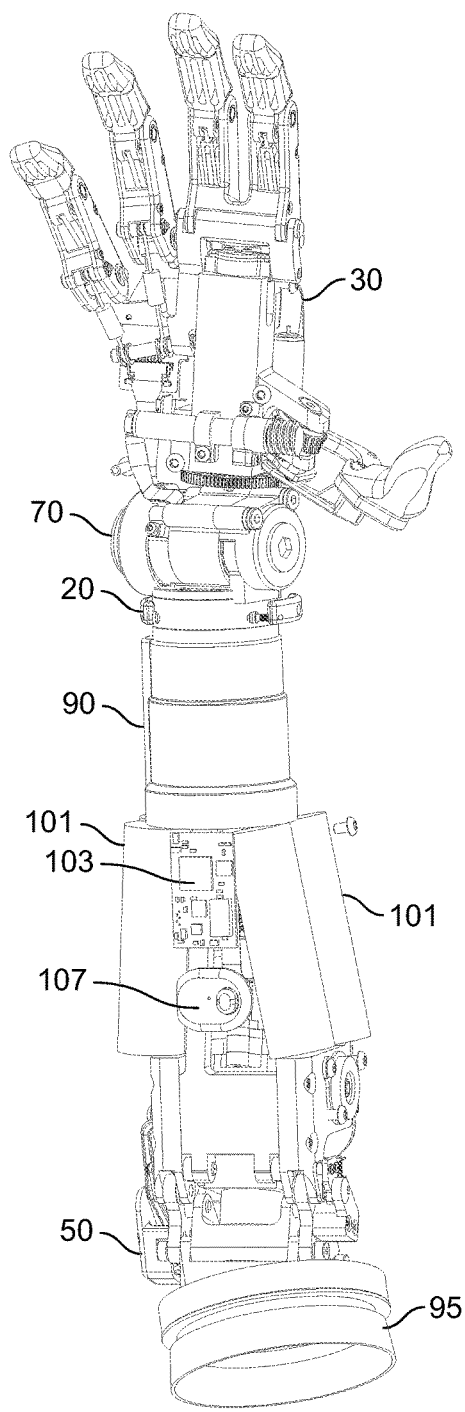
FIG. 3 is a cut-away anterior view of the prosthetic limb, according to an embodiment.
Figure 4:
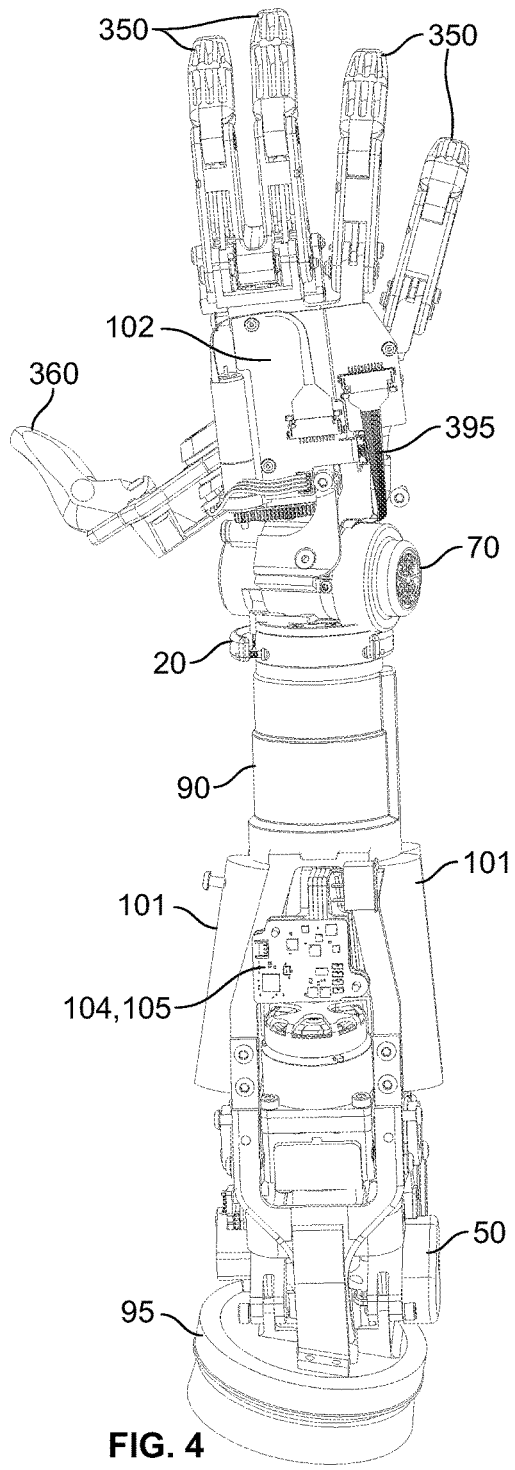
FIG. 4 is a cut away posterior view of the prosthetic limb, according to an embodiment.

FIG. 3 shows a cut-away anterior view of the limb 10 and FIG. 4 shows a cut-away posterior view of the limb 10. Four batteries 101 that provide power to the limb 10 are housed in a forearm 150. In one embodiment, each battery 101 is a 14.8V Tenergy Li-Ion 18500 Cylindrical 3.7V 1400 mAh with tabs from All-Battery. In other embodiments, the batteries 101 could be housed externally to the limb 10, for instance on a user's belt. As shown in FIG. 4, a master controller 102 is housed on top of the hand 30.

In one embodiment, the master controller 102 is housed in the forearm 150 and controls the movement of fingers 350, a thumb 360, the wrist flexor 70, the wrist rotator 90, and the elbow 50. The master controller 102 may be programmed with a pattern recognition module, a direct control module, or another module known in the art in order to cause different components of the limb 10 to move. In one embodiment, the master controller 102 is programmed with a control module, modified from small motor controller software obtained under license from the Johns Hopkins University Applied Physics Laboratory (Laurel, Md.) to allow CAN communication. The master controller 102 may record user signals from sensors 26 coupled to a user's socket 25. The sensors 26 may be EMG sensors or other appropriate sensors. The master microcontroller 102 uses a 4-wire CAN bus to communicate the movements of the components of the limb 10.

A flexible circuit 395 is coupled to the master controller 102 for communication to and from the master controller 102. Where the limb 10 makes use of pattern recognition control using EMG signals, the master controller 102 communicates with the sensors 26 in the user's socket 25 (not shown) to train the pattern recognition control module and to operate the limb 10. A training switch 107 switches the limb 10 between a training mode, in which information collected from the sensors 26 train the pattern recognition module, and an operating mode, in which information collected from the sensors 26 are used by the master controller 102 to move different components of the limb 10, including the elbow 50, the wrist rotator 90, the wrist flexor 70, the fingers 350, and the thumb 360. Wire connectors for power, ground, and communication signals (not shown) extend from the proximal end of the socket connector 95 for connection with the appropriate electrodes at the user's socket 25.

As shown in FIG. 3, in one embodiment the forearm 150 also may house a secondary controller 103. In one embodiment, the secondary controller 103 may control the movement of the elbow 50 and the wrist rotator 90. Such a configuration can be useful when the universal coupler 20 is released and the master controller 120 is separated, along with the wrist flexor 70 and the hand 30, from the rest of the limb 10. An elbow board 104 controls an exterior-rotor motor 510 and a rotator board 105 controls an exterior-rotor motor 910.

Hand.

Figure 5:
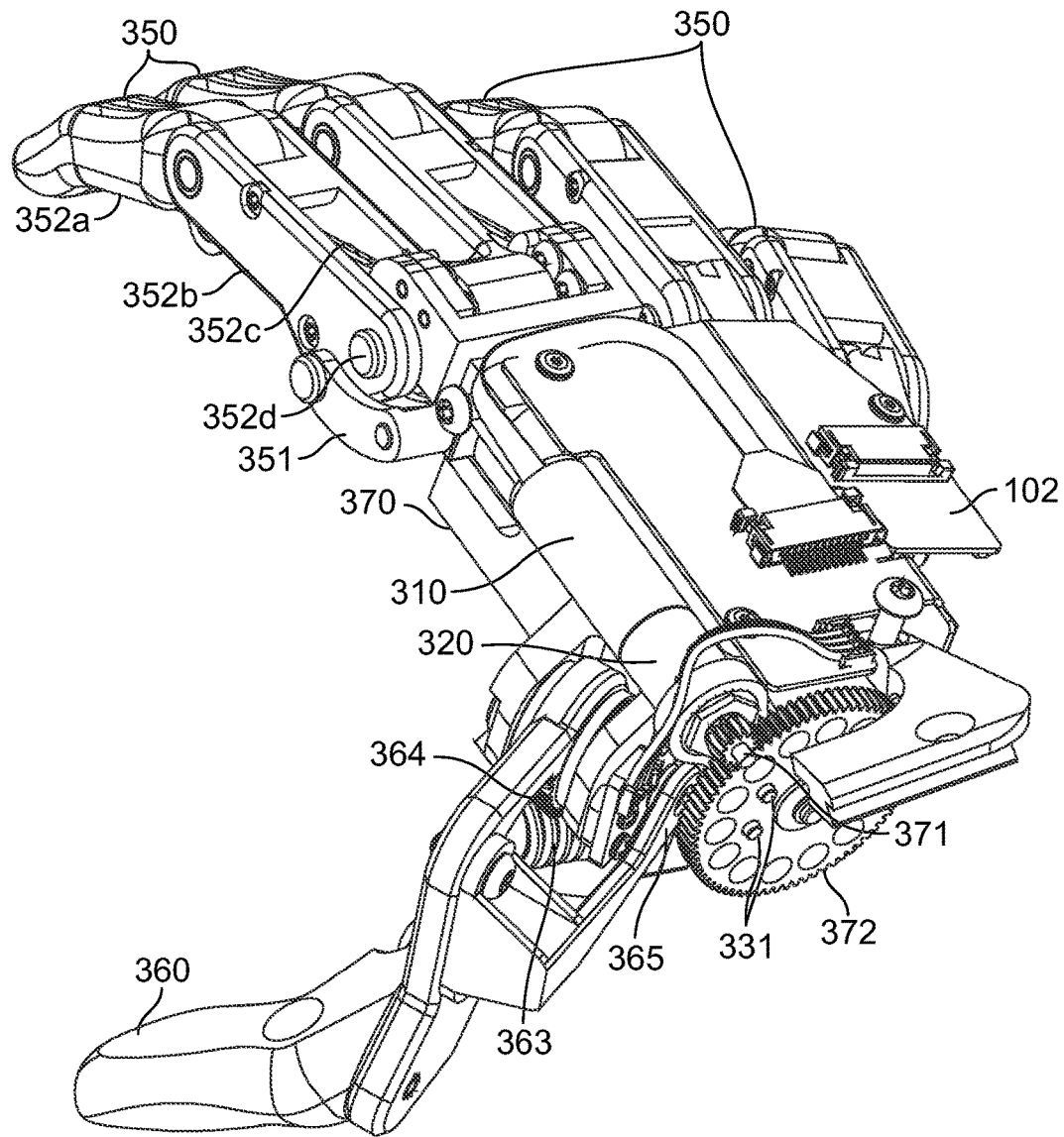
FIG. 5 is a posterior view of a hand of the prosthetic limb, according to an embodiment.

As shown in FIG. 5, the hand 30 is a modular component that comprises an endoskeleton 370, the fingers 350, the thumb 360, hand-motor motor-amplifiers (not shown), and the master controller 102. The endoskeleton 370 is fastened to the output of the wrist flexor 70. In one embodiment, the endoskeleton 370 is made of aluminum or another suitable lightweight material. The endoskeleton 370 supports the fingers 350 and the thumb 360. The endoskeleton 370 also houses the hand-motor motor-amplifiers and a hand microcontroller (not shown), which are embedded in the master controller 102. The hand 30 further comprises a rotor motor 310, a planetary gear transmission 320, a non-backdrivable clutch 330, a differential roller screw 340, and a finger linkage 355. In one embodiment, the rotor motor 310 is a brushless interior rotor motor and is coupled to the planetary gear transmission 320.

Figure 6:
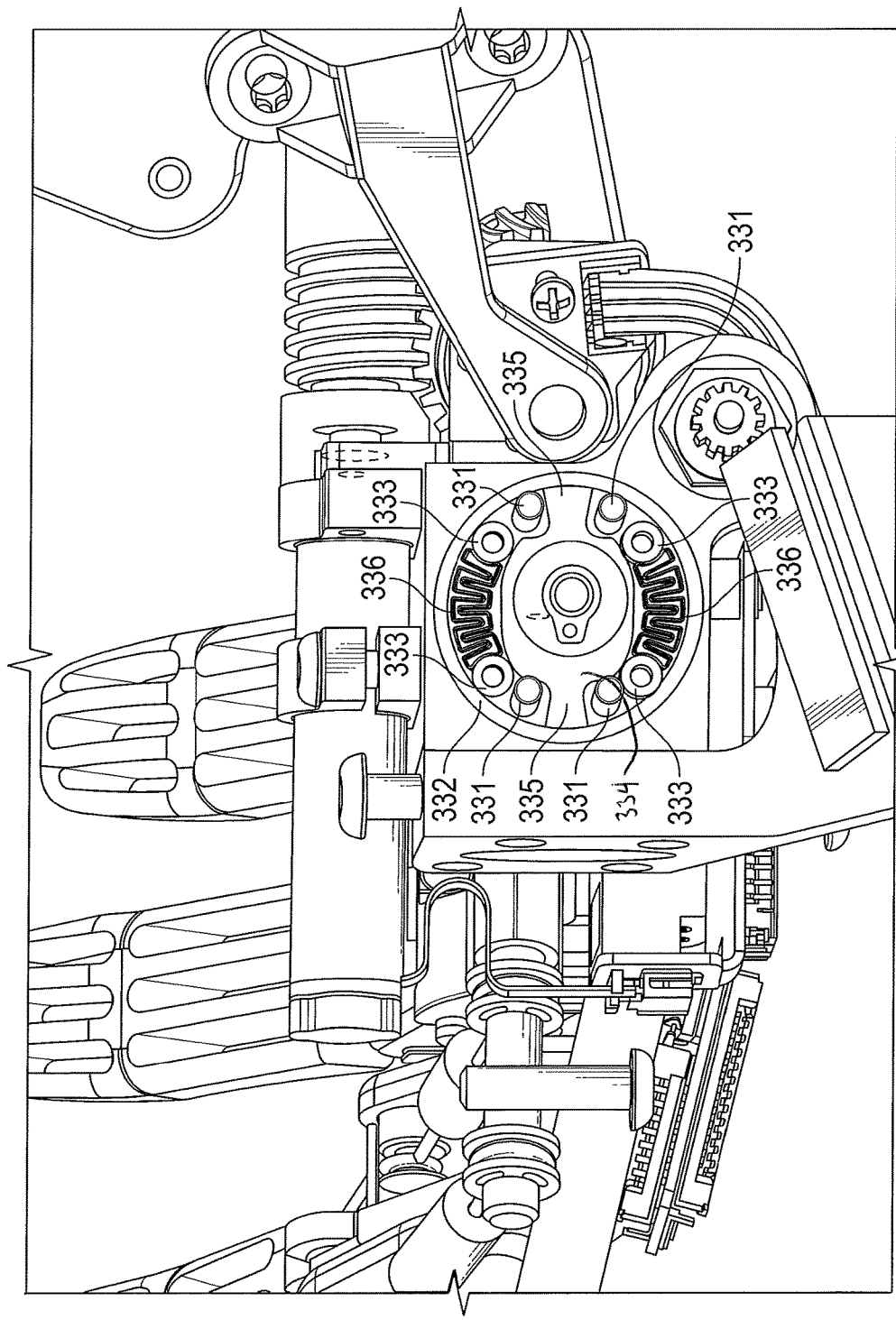
FIG. 6 is a proximal view of the hand of the prosthetic limb, showing a possible implementation of a non-backdrivable clutch.

The rotor motor 310 and the planetary gear transmission 320 actuate a pinion gear 371, which actuates a finger gear 372. The finger gear 372 is connected to pins 331, which extend into a clutch 330 to drive the clutch 330. FIG. 6 shows the clutch 330 as a non-backdrivable clutch located at the proximate end of the hand 30. The clutch 330 in this embodiment comprises an annulus 332, rollers 333, an output cam 334, and springs 336. The springs 336 ensure that the rollers 333 are in contact with the annulus 332 when the clutch 330 is not being driven. As a finger gear 372 turns to actuate the clutch 330, the pins 331 push the rollers 333 out of contact with the annulus 332, allowing the output cam 334 to turn. The pins 331 also engage protrusions 335 on the output cam 334. Motion of the output cam 334 occurs when the pins 331 push the rollers 333 out of contact with the annulus 332 before they engage the protrusions 335 on the output cam 334. If movement is attempted from the output side of the clutch 330 without pushing the rollers 333 out of the way, the jam angle between the grounded annulus 332, the rollers 333, and the output cam 334 prevents motion from occurring. The annulus 332 includes a mechanical fuse (not shown) to prevent excessive torque applied to the fingers 350 from damaging the rotor motor 310. For instance, if the user falls on the hand 30, the mechanical fuse fails and may be replaced with relative ease.

Figure 7:
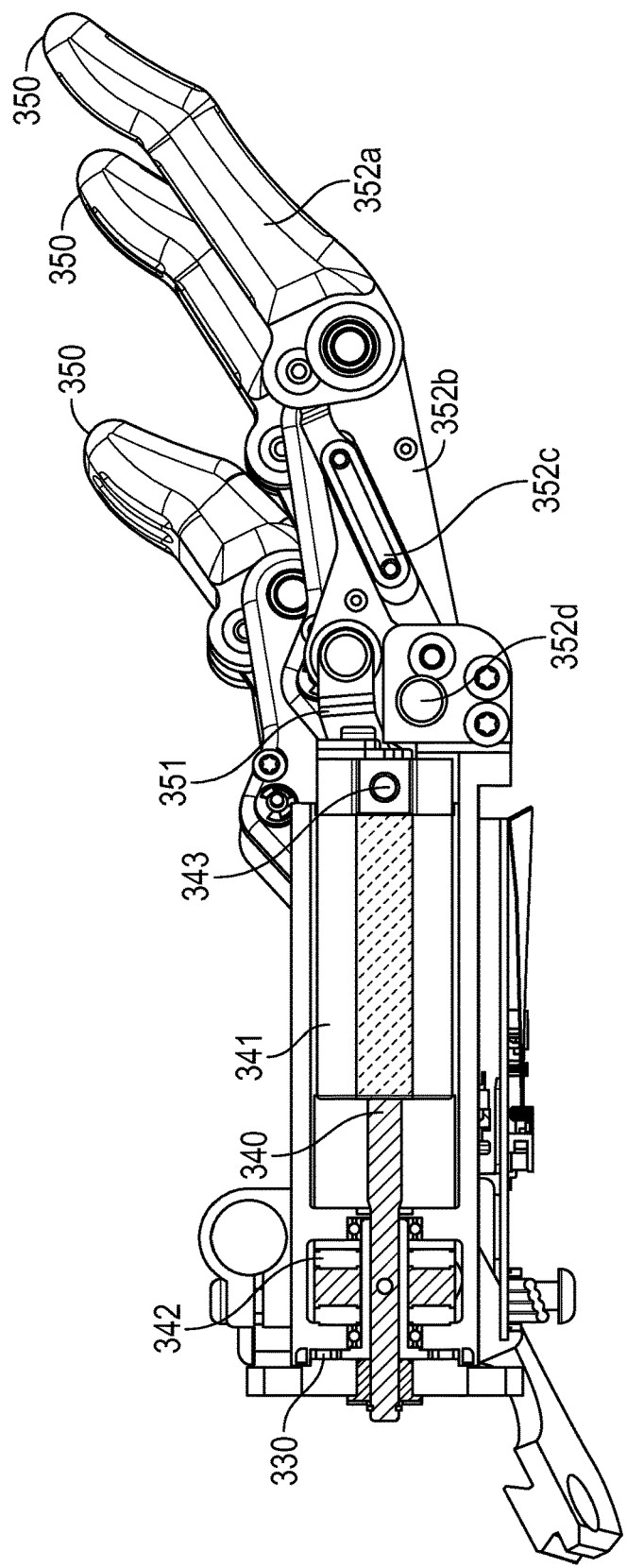
FIG. 7 is a cross-section lateral view of the hand of the prosthetic limb, according to an embodiment.

FIG. 7 is a cross-section lateral view of the hand 30. The differential roller screw 340 is housed in a casing 341 that prevents bending moments upon the differential roller screw 340. A thrust bearing 342 prevents axial loads from the differential roller screw 340 from being transmitted to the clutch 330. The differential roller screw 340 is affixed via a pivot 343 to a linkage connector 351, which in turn connects to a linkage 352 of the fingers 350. The linkage 352 comprises a first link 352a, a second link 352b, a third link 352c, and a link 352d to ground, as shown in FIG. 5. The rotational motion of the output cam 334 causes the differential roller screw 340 to thread through the casing 341, causing a roller screw nut 343 to move distally or proximally in response to motion of output cam 334. The linkage connector 351 moves in response to movement from the roller screw nut 343, which in turn activates the linkage 352, causing the fingers 350 to flex and extend.

Figure 8:
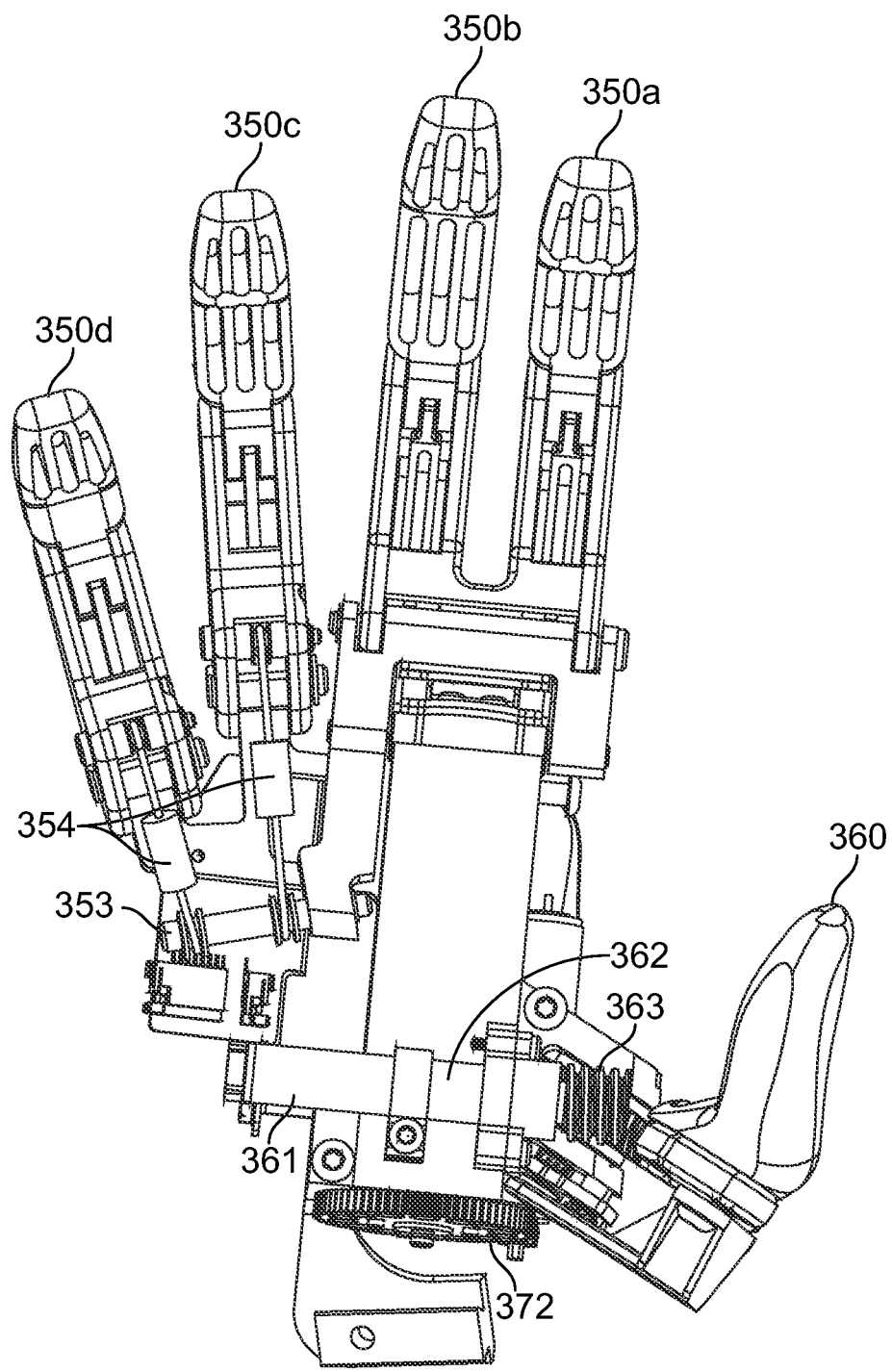
FIG. 8 is an anterior view of the hand of the prosthetic limb, according to an embodiment.

FIG. 8 shows an anterior view of the hand 30. A side arm 353 projects from the differential roller screw 340 to transmit motion to a ring finger 350c and a pinky finger 350d via lateral finger springs 354. The linkage 352 transmits motion from the differential roller screw 340 to the fingers 350 without creating a bending moment on the differential roller screw 340. FIG. 8 also shows the fingers 350. Each finger 350a, 350b, 350c, and 350d employs the linkage 352—a four-bar linkage in the illustrated embodiment. The linkage 352 couples flexion of the metacarpophalangeal joint ("MCP") to flexion of the proximal interphalangeal joint ("PIP") joint. This four-bar linkage geometry is optimized to provide maximal pinch-force to motor torque ratio, within spatial and mechanical constraints, while generating motion that is anatomically natural. Linkages for each finger 350 are shown at FIG. 5, where the linkage 352 for the index finger 350a is labeled. The link connecting the frame to the distal phalange in each finger is designed with longitudinal compliance, resulting in approximately 5 degrees of compliance at the PIP joint for the index finger 350a and the middle finger 350b. In one embodiment, the proximal phalanges of the index finger 350a and the middle finger 350b are fused together for rigidity. The ring finger 350c and the pinky finger 350d are each independently hinged, and coupled via compliant springs 354 to the side arm 353. Having the ring finger 350c and the pinky finger 350d independently hinged allows for them to move with the index and middle fingers 350a and 350b, and to generate a conformal grasp by the hand 30.

Thumb.

Figure 9:
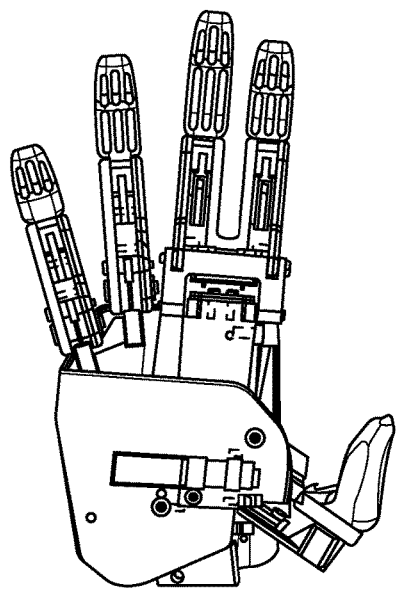
FIG. 9 shows the hand of the prosthetic limb in a relaxed posture, according to an embodiment.
Figure 10:
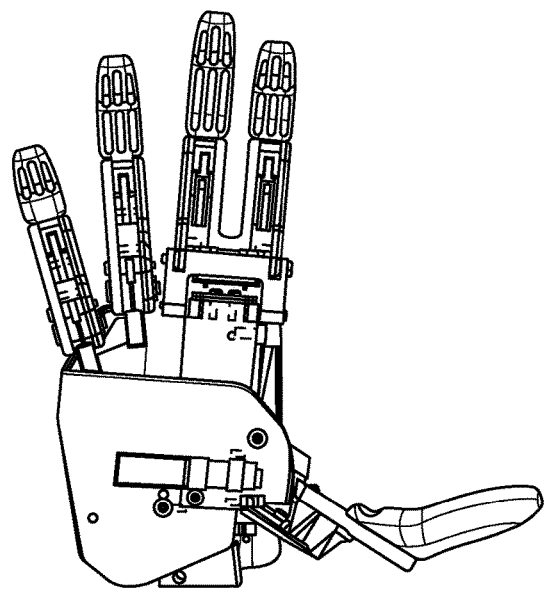
FIG. 10 shows the hand of the prosthetic limb in a palm-flat posture, according to an embodiment.
Figure 11:
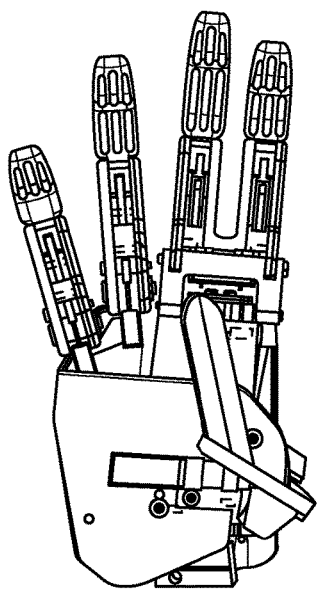
FIG. 11 shows the hand of the prosthetic limb in a chuck grip posture, according to an embodiment.
Figure 12:
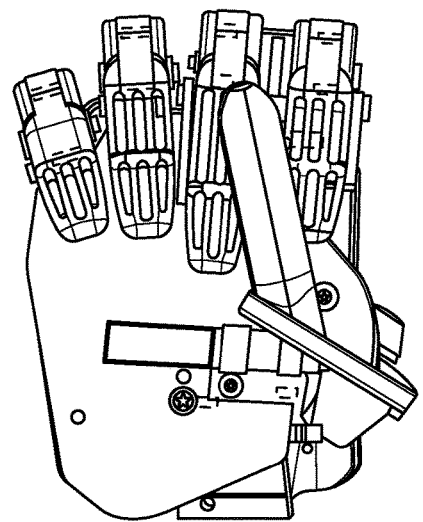
FIG. 12 shows the hand of the prosthetic limb in a cylindrical grip posture, according to an embodiment.

In one embodiment, the thumb 360 comprises its own rotor motor 361 coupled to a planetary gear 362. According to an embodiment, the thumb 360 is independently powered from the finger 350 and is driven by the rotor motor 361 and planetary gear 362 so as to act independently of the fingers 350. Having an independent thumb 360 increases the stability of the gripping ability of the hand 30. The thumb 360 has a single degree of freedom. In one embodiment, the rotor motor 361 is a brushless interior rotor motor, model EC 10 from Maxon Precision Motors, Inc. (Fall River, Mass.), which is coupled to the planetary gear transmission 362 offered by the same company. Movement is transmitted from the planetary gear transmission 362 to the thumb 360 via a worm pinion 363 that interfaces with a worm gear 364. In one embodiment, the worm gear 364 is a custom, off-axis helical worm gear, made of brass. In one embodiment, shown in FIG. 5, the worm gear 364 is positioned posterior to the worm pinion 363. The worm gear 364 converts motion from the worm pinion 363 to the rotation axis of the thumb 360. The axis of the thumb 360 is positioned such that the thumb 360 may provide multiple different hand postures with a single degree of freedom. These postures include relaxed (shown at FIG. 9), palm-flat (shown at FIG. 10) chuck grip (shown at FIG. 11), and cylindrical grip (shown at FIG. 12). To fit the rotor motor 361 and the thumb transmission (including the planetary gear 362 and the worm pinion 363) within the hand 30 profile, the axis of the worm pinion 363 is skewed by approximately 20 degrees. The tooth profile of the worm gear 364 allows for proper meshing with the skewed position of the worm pinion 363. A position sensor 365 senses the position of the thumb 360, and information from the position sensor 365 is used by the master controller 102 for position control of the thumb 360. In one embodiment, the position sensor 365 is a magnetic hall-effect sensor, shown in FIG. 5.

Wrist.

In an embodiment, the wrist of the limb 10 has two degrees of freedom: rotation from the wrist rotator 90 and flexion from the wrist flexor 70. Each of the wrist rotator 90 and the wrist flexor 70 is a wrist component. The wrist rotator 90 comprises an exterior-rotor motor 910, a planetary gear transmission 920, a non-backdrivable clutch 930, and a cycloid transmission 940. In one embodiment, shown in FIGS. 1-4, the wrist rotator 90 has an outer diameter of 20 mm and a length of 13 mm. In one embodiment, insulation material is made of Paralyne with an insulation thickness of 0.0508 nm. The wrist rotator may utilize a supply voltage of 14.8V and a supply current of 4 A from batteries 101, and include WYE termination and a net fill factor of 65%. Seals may be applied to the wrist flexor 70 and the wrist rotator 90 to make them water-resistant.

The wrist rotator 90 is powered by the exterior-rotor motor 910, which in one embodiment is a DC brushless motor. Magnets are placed at the ends of each tooth, radial to the center of the motor's stator. In one embodiment, 14 magnets are placed distally around the center of the stator. The magnets are arranged in an alternating pole arrangement, where each magnet's pole is opposite to its neighbor. Each stator tooth is wrapped with three-phase, single span windings resulting in three sets of wires looped around the stator. The winding pattern is AacCBbaACcbB, where capital letters denote clockwise winding and lower-case letters denote counter-clockwise winding, and A, B, and C denote the three phases.

In one embodiment, the exterior-rotator motor 910 is controlled by the master controller 102. In other embodiments, where the master controller 102 is not available in the hand 30, the exterior-rotator motor 910 may be controlled by the secondary controller 103. The control module on either the master controller 102 or the secondary controller 103 times when current should run through each motor winding of the exterior-rotator motor 910 and sends a signal to FETs to drive the exterior-rotator motor 910.

Figure 13:
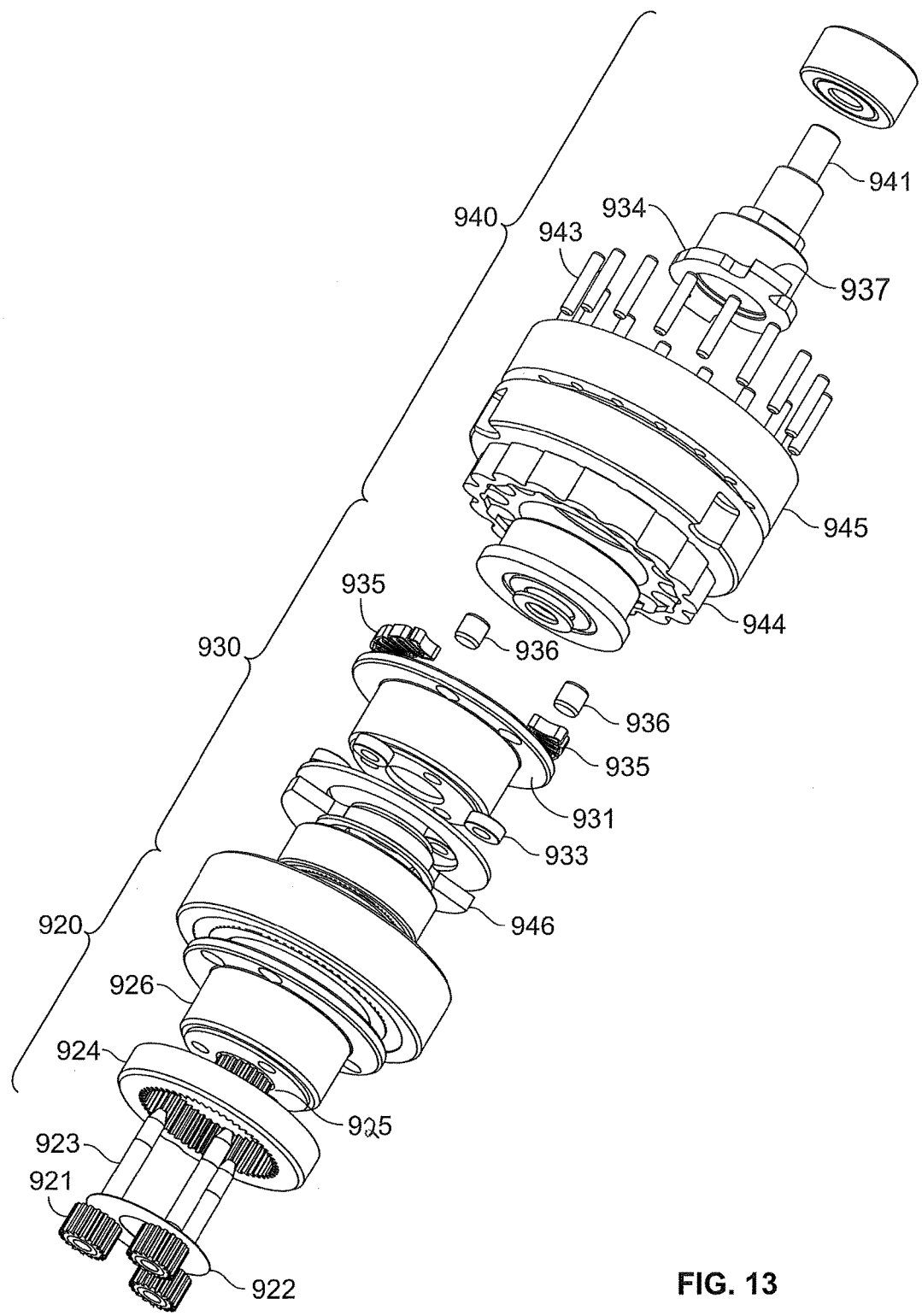
FIG. 13 is an exploded view of the planetary gear transmission, non-backdrivable clutch, and cycloid transmission components of the wrist rotator of the prosthetic limb, according to an embodiment.

The exterior-rotator motor 910 is connected to a planetary gear transmission 920, shown in FIG. 13. The planetary gear transmission 920 comprises a grounded annulus 924, a sun gear (input) 925 fastened to the motor output, planetary gears 921, and a carrier plate (output) 926. In one embodiment, the planetary gear transmission 920 is a modified 1-stage planetary gear modified from a stock MicroMo gear (16/7 246:1). In other embodiments, the planetary gear transmission 920 may comprise a 2-stage planetary gear.

The output of planetary gear transmission 920 is coupled to a non-backdrivable clutch 930, also shown at FIG. 13. In one embodiment, the non-backdrivable clutch 930 allows motion from the planetary gear transmission 920 to be transmitted to the non-backdrivable clutch 930 output in either direction, clockwise or counter-clockwise, but inherently prevents any additional movement from the output of the non-backdrivable clutch 930 to be transmitted to the input of the cycloid transmission 940, thus allowing the actuation unit (i.e., the planetary gear transmission 920, the non-backdrivable clutch 930, and the cycloid transmission 940) to maintain a position without requiring constant power consumption from the motor, as described further in M. Controzzi, C. Cipriani, M. C. Carrozza. Miniaturized non-back-drivable mechanism for robotic applications, Mechanism and Machine Theory, Elsevier, vol. 45, no. 10, pp. 1395-1406, 2010. This locking feature allows a user to carry a heavy object, such as a grocery bag, without the batteries 101 needing to supply power to the motors to keep the object lifter. As a result, the wrist rotator 90 is capable of passively holding more force than it can actively generate.

As shown in FIG. 13, the non-backdrivable clutch 930 comprises an input plate 931, a grounded annulus 932 (encapsulating the clutch 930, and not shown), four rollers 933, an output cam 934, and two springs 935 that ensure the rollers 933 are in contact with the ground. Pins 936 on the input plate 931 push the rollers 933 out of contact with the grounded annulus 932. The pins 936 on the input plate 931 also engage protrusions 937 on the output cam 934. Motion of the non-backdrivable clutch 930 occurs when the pins 936 push rollers 933 out of contact with the grounded annulus 932 before the pins 936 engage the protrusions 937 on output cam 934. If movement is attempted from the output side of the non-backdrivable clutch 930 without pushing the rollers 933 out of the way, the jam angle between the grounded annulus 932, the rollers 933, and the output cam 934 prevents motion of the non-backdrivable clutch 930 from occurring.

Figure 14:
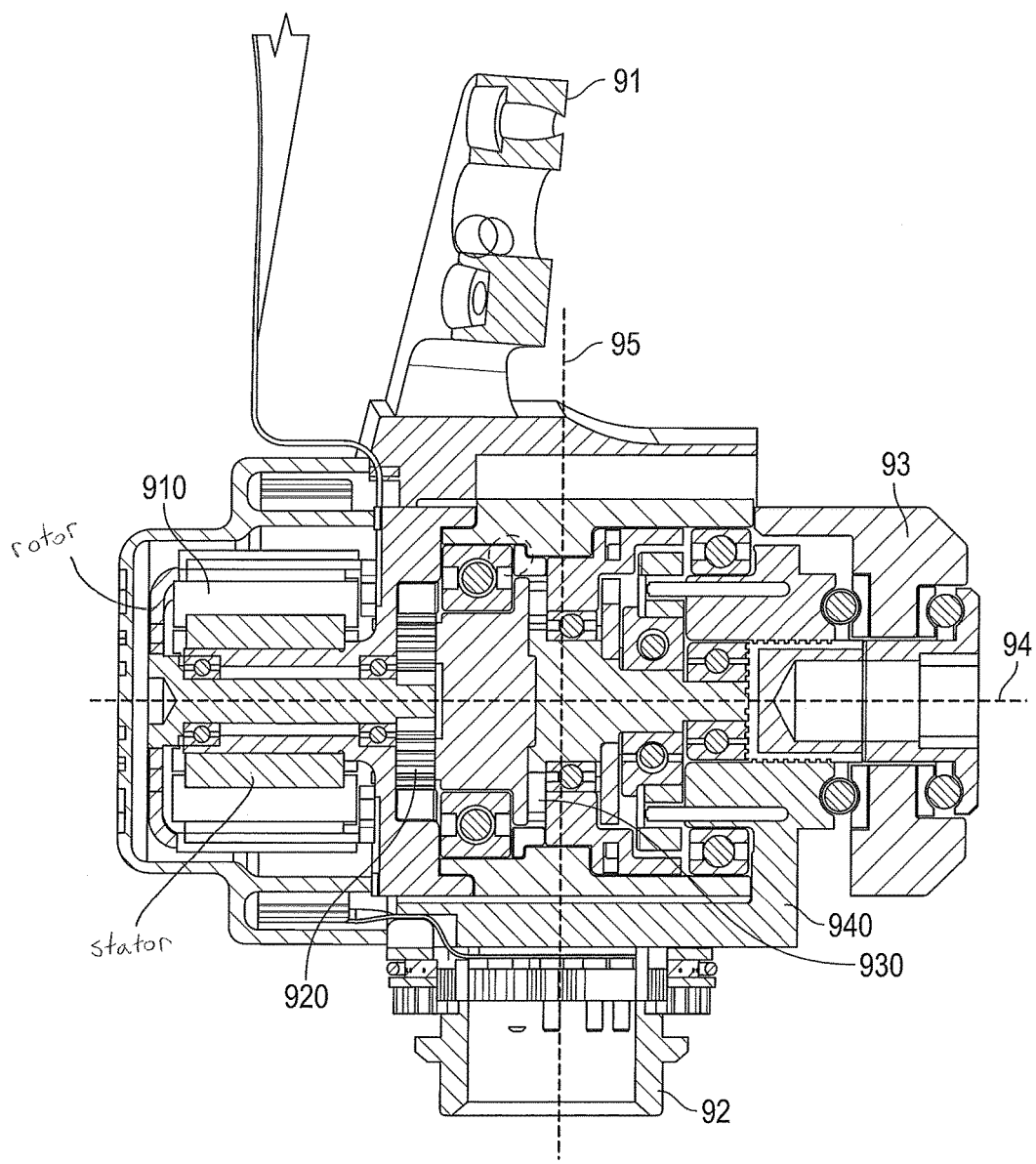
FIG. 14 is a cross-section view of the wrist rotator of the prosthetic limb, according to an embodiment.

Still with respect to FIG. 13, the output of the non-backdrivable clutch 930 is connected to a cycloid transmission 940, as described further in references J. W. Sensinger, "Efficiency of High-Sensitivity Gear Trains, Such as Cycloid Drives," J. Mech. Des. 135(7), 071006 (2013) (9 pages); Del Castillo, J. M., 2002, "The Analytical Expression of the Efficiency of Planetary. Gear Trains," Mech. Mach. Theory, 37(2), pp. 197-214, 2002; and J. W. Sensinger, Unified Approach to Cycloid Drive Profile, Stress, and Efficiency Operation," J. Mech. Des. 132(2), 024503 (2010) (5 pages). The cycloid transmission 940 comprises a grounded annulus (not shown) that houses a set of freely spinning rollers 943, an eccentric input cam 941, a cycloid disk 944, and an output carrier plate 945. In one embodiment, parameters of the cycloid transmission 940 may be optimized so that the torque ratio of the cycloid transmission 940 is 16:1 and its outer diameter is 23 mm. As a result of these constraints, the input eccentricity of the cycloid transmission 940 is 0.57 mm, its roller diameter is 1 mm, and its roller offset diameter is 20 mm. These parameters are optimized to provide minimum radial loading while maintaining a design without undercutting the gear-tooth profile. The cycloid disk 944 profile may be determined using the methods set out in reference J. W. Sensinger, Unified Approach to Cycloid Drive Profile, Stress, and Efficiency Operation," J. Mech. Des. 132(2), 024503 (2010) (5 pages). A counter-weight 946 is also shown in FIG. 13. In an embodiment, the counter-weight 946 is attached to the eccentric input shaft 947 at 180° out of phase with the cycloid disk 944, so as to cancel out oscillatory vibrations. FIG. 14 displays a cross section view of the transmission components of the wrist rotator 90. It should be understood that although one embodiment of planetary gear transmission 920, non-backdrivable clutch 930, and cycloid transmission 940 is detailed here, other embodiments would be apparent to one of ordinary skill in the art. As shown in FIG. 14, the plate 91 may be configured to be coupled to the frame of the hand 30. Housing 93 provides a cover to the wrist rotator 90 and may be made of plastic or another suitable material. A connector 92 may be configured to connect to the output of the wrist flexor 70, so as to transfer the flexion/ extension motion produced by the wrist flexor 70 through the wrist rotator 90 and to the hand 30, along a flexor axis 95, shown in FIG. 14. Actuation of the transmission of the wrist rotator 90 causes the wrist rotator 90 to rotate around a rotator axis 94 along the a cycloid output 750 (shown in FIG. 2).

In one embodiment, contribution of increasing the torque was balanced between the torque ratios of the planetary gear transmission 920 (3.71:1) and the cycloid transmission 940 (16:1) using the known efficiency of both mechanisms as set out in J. W. Sensinger, "Efficiency of High-Sensitivity Gear Trains, Such as Cycloid Drives," J. Mech. Des. 135(7), 071006 (2013) (9 pages) and Del Castillo, J. M., 2002, "The Analytical Expression of the Efficiency of Planetary. Gear Trains," Mech. Mach. Theory, 37(2), pp. 197-214, 2002, in order to maximize the total torque produced by wrist rotator 90 while ensuring a reasonably low stress on the components of the wrist rotator 90.

The distal end of the wrist rotator 90 includes a bulls-eye pattern of four copper ring interfaces, for transmitting four signals across the axis of rotation of the wrist rotator 90. In one embodiment, one of the interfaces transmits power, two of the interfaces transmit communication signals, and one of the interfaces acts as an electrical ground. The proximal end of the wrist flexor 70 includes multiple conductive pins. When the wrist flexor 70 is coupled to the wrist rotator 90, and the limb 10 is in training mode or operating mode, the multiple conductive pins provide power from the batteries 101 to the wrist flexor 70 and the hand 30. The concentric pattern of copper ring interfaces, and their connection to the spring-loaded pins, allow for continuous operation of the limb 10 while the wrist rotator 90 is rotating. The distal portion of the wrist rotator 90 is the proximal side of the universal coupler 20, which allows the wrist to be interchanged with a variety of hand units. In other embodiment, a battery powering hand 30 could be housed in hand 30.

Figure 2:
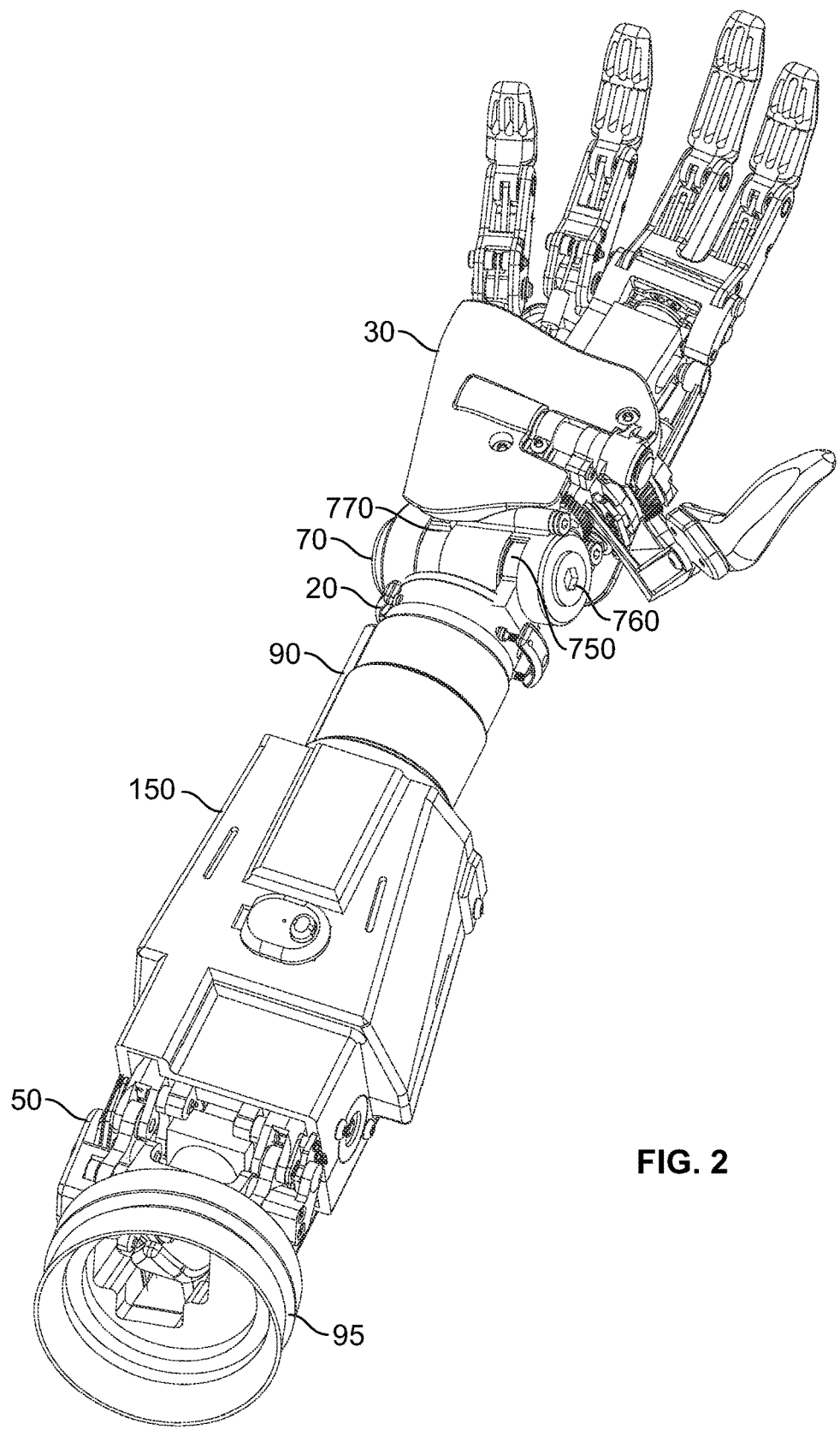
FIG. 2 is an anterior view of a prosthetic limb, according to an embodiment.

Wrist flexor. In an embodiment, the wrist flexor 70 utilizes the same drivetrain design used in the wrist rotator 90, described herein, including the exterior-rotor motor 910, the planetary gear transmission 920, the non-backdrivable clutch 930, and the cycloid transmission 940. The wrist flexor 70 uses a flexible circuit (not shown) to pass electrical signals, including signals to and from the master controller 102 and the secondary controller 103, across its axis of rotation. FIG. 2 shows an anterior view of the limb 10, including a view of the wrist flexor 70. The wrist flexor 70 has a range of motion limited by a mechanical stop 770. The wrist flexor 70 is of modular design and is coupled to the wrist rotator 90 by the universal coupler 20. The proximal portion of the wrist flexor 70 is the distal portion of the universal coupler 20. The wrist flexor 70 includes a shear pin (not shown) that breaks at a specified excessive torque, which limits damage to the wrist flexor 70 if the user falls and lands on the wrist flexor 70 or if the wrist flexor 70 is the subject of other accidental force.

The rotation axis of the wrist flexor 70 actuates primarily in the direction of flexion and extension. The axis location is skewed by 10-30 degrees to provide radial/ulnar deviation in addition to the primary flexion/extension directions of motion. This results a movement known as a dart-thrower motion that has been found to be the most common movement in activities of daily living. The wrist flexor 70 and the wrist rotator 90 could be coupled to the hand 30, or to another commercially available prosthetic hand, such as the Transcarpal Hand offered by Ottobock (Duderstadt, Germany).

Elbow.

In one embodiment, the elbow 50 is a modular unit that provides flexion and extension about the elbow axis. The elbow 50 generates movement of the forearm 150 in response to a command of the user.

Figure 15:
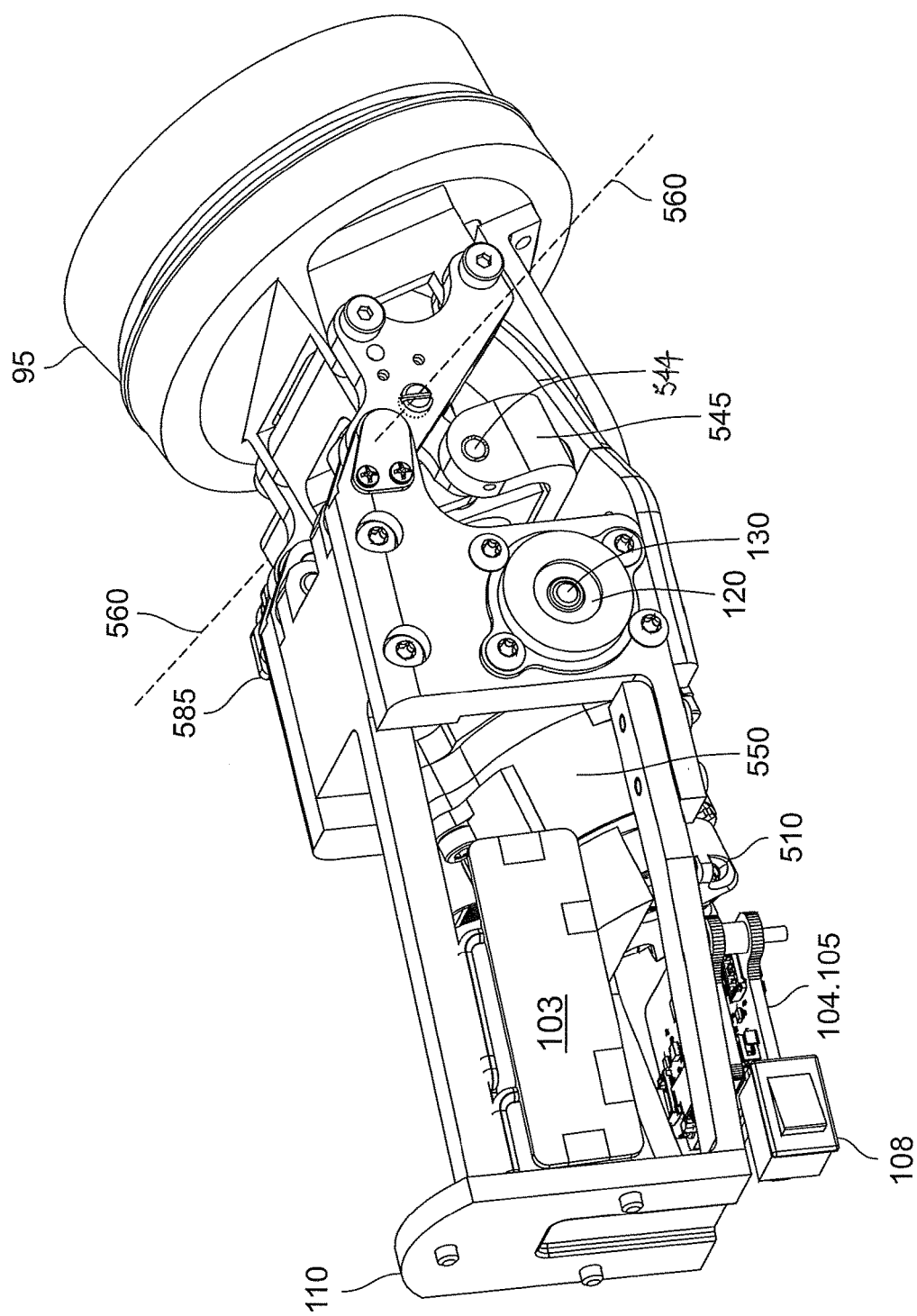
FIG. 15 is a lateral view of the elbow of the prosthetic limb, according to an embodiment.

FIG. 15 shows a lateral view of the elbow 50. In one embodiment, the elbow 50 is connected to the frame 110, which has openings for the batteries 101 (not shown in FIG. 15). An on/off switch 108 for the limb 10 is coupled to the frame 110. The frame 110 surrounds a transmission housing 550 and supports an elbow hinge joint 130 and a bushing 120. A position sensor 585 indicates rotational movement of elbow 50. In one embodiment, the position sensor 585 is a magnetic hall-effect sensor. The axis of rotation of the elbow 50 is shown by the line 560. The distal end of the elbow 50 is coupled to the socket connector 95. The flexion axis is offset ventrally to the limb center. This allows additional components to be packaged in the elbow space, but leaves a gap when the elbow is fully flexed. This gap may be covered by a compliant covering, such as rubber or fabric.

Figure 16:
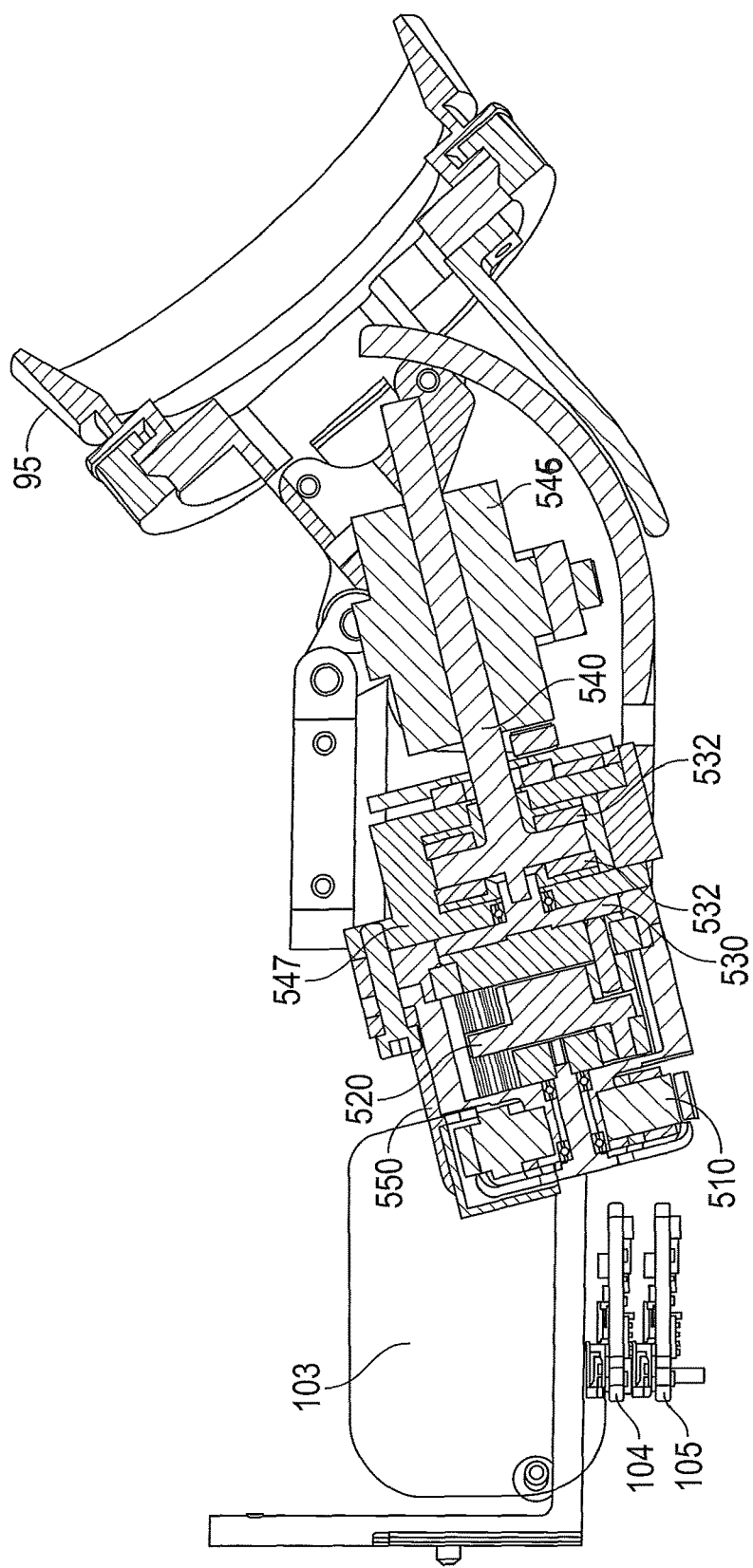
FIG. 16 is a cross-section view of the elbow of the prosthetic limb, according to an embodiment.

FIG. 16 shows a cross-section view of the elbow 50. The elbow 50 comprises an exterior-rotor motor 510. In an embodiment, the exterior-rotor motor is of the same design as the exterior-rotor motor used in the wrist rotator 90. The elbow 50 further comprises a planetary gear transmission 520, which, as shown in FIG. 16, is a two-stage planetary transmission. In an embodiment, the planetary gear transmission 520 is modified from a stock gear offered by MicroMo (Clearwater, Fla.) that increases output torque while reducing speed. The elbow 50 further comprises a non-backdrivable clutch 530 coupled to a differential roller screw 540. In general, differential roller screws such as the differential roller screw 540 are useful to convert rotary motion to linear motion, as it has high efficiency (86%) similar to a ball screw, yet can withstand high axial forces, similar to lead screws, that result from the loads experienced by the arm. In one embodiment, the differential roller screw 540 converts the rotary motion of the non-backdrivable clutch 530 to linear motion. In one embodiment, a non-backdrivable differential roller screw may be used. A thrust housing 547 pushes against the differential roller screw 540 when the differential roller screw 540 actuates to flex the elbow 50.

Figure 17:
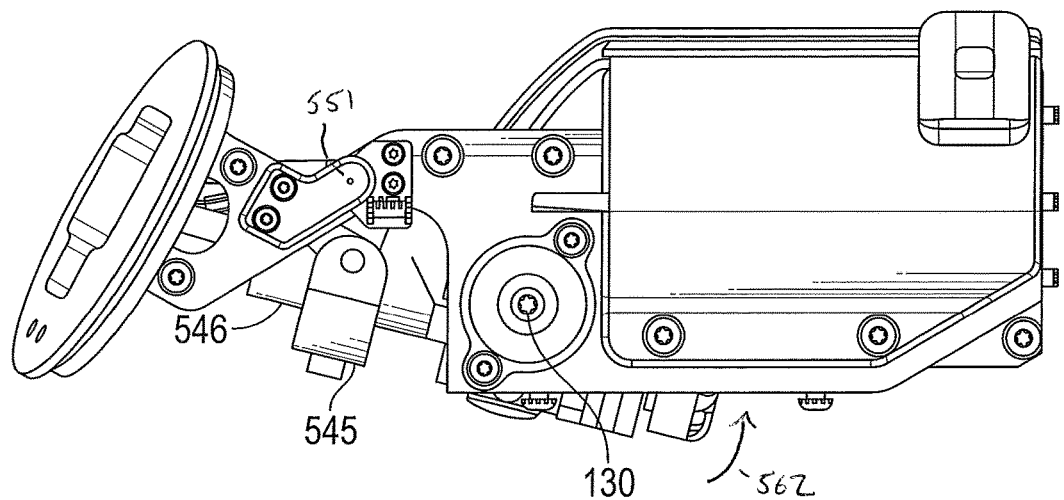
FIG. 17 shows the elbow of the prosthetic limb in an extended position, according to an embodiment.
Figure 18:
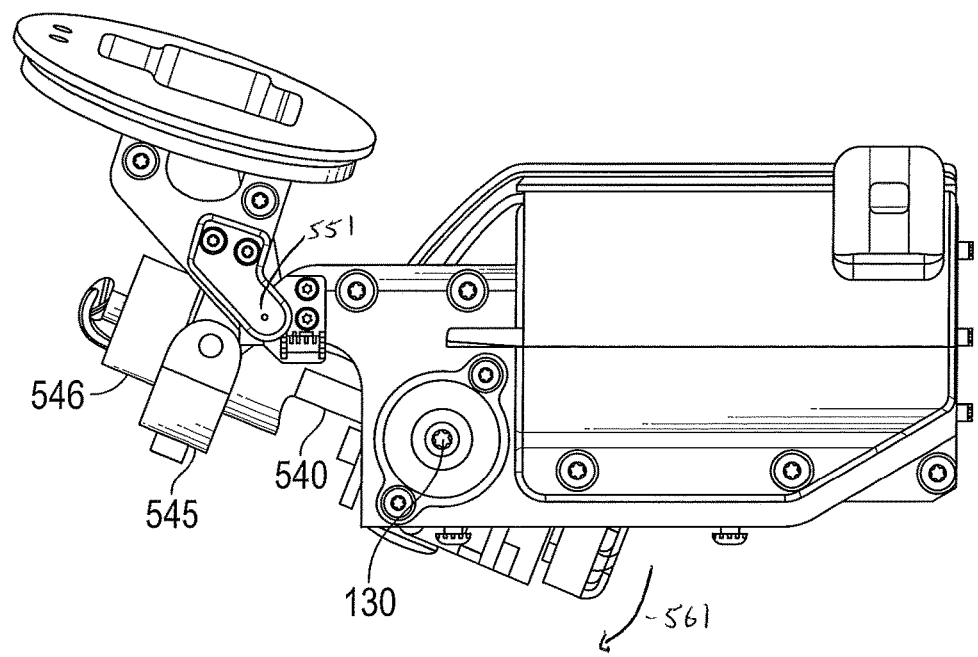
FIG. 18 shows the elbow of the prosthetic limb in a flexed position, according to an embodiment.

A roller screw nut 546 of the differential roller screw 540 pivots about hinge joint 130 and nut pivot 546, so that the differential roller screw 540 experiences axial loads but not bending moments. FIG. 17 shows elbow 50 extended and FIG. 18 shows elbow 50 flexed, with differential roller screw 540 pivoting about the hinge joint 130. The hinge joint 130 is encased in the bushing 120. In one embodiment, the bushing 120 is made of a nonlinear compliant material, such as rubber, rather than of a rigid material. When made of a nonlinear compliant material, the bushing 120's stiffness provides the elbow 50 with joint compliance similar to that of able-bodied persons when their elbows swing freely during walking. As a result, a user who walks while wearing limb 10 using a non-compliant bushing 120 experiences a more natural swinging movement. Additionally, the nonlinear nature of the compliance prevents the joint of the elbow 50 from deforming too far, such as when a user raises the limb 10 over her head or uses the limb 10 to push herself out of her seat.

Figure 19:
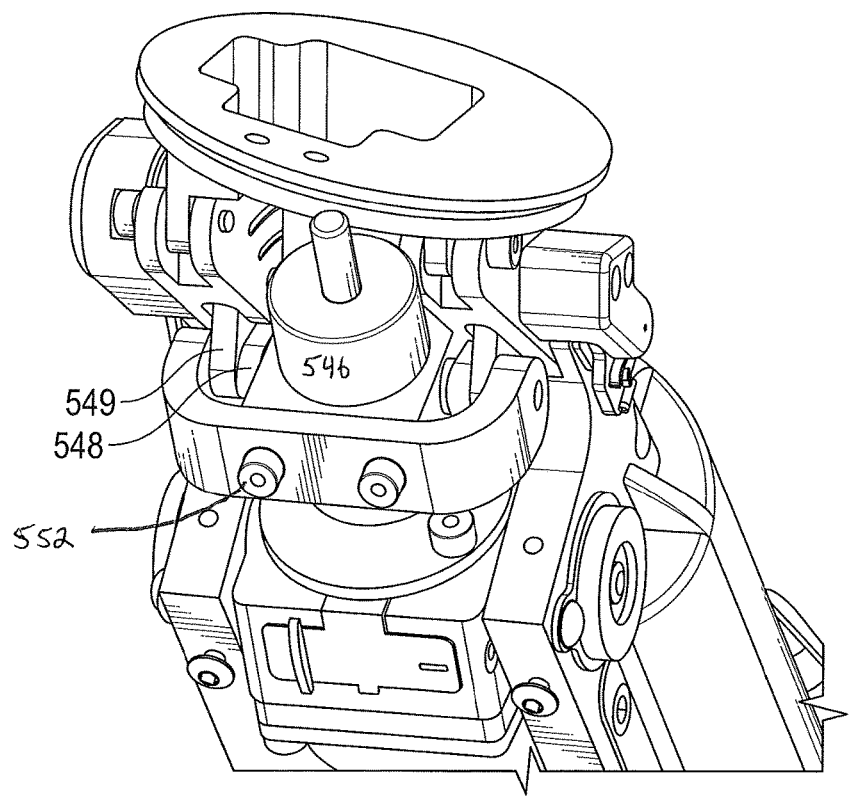
FIG. 19 shows a perspective view of the elbow of the prosthetic limb, according to one embodiment.
Figure 20:
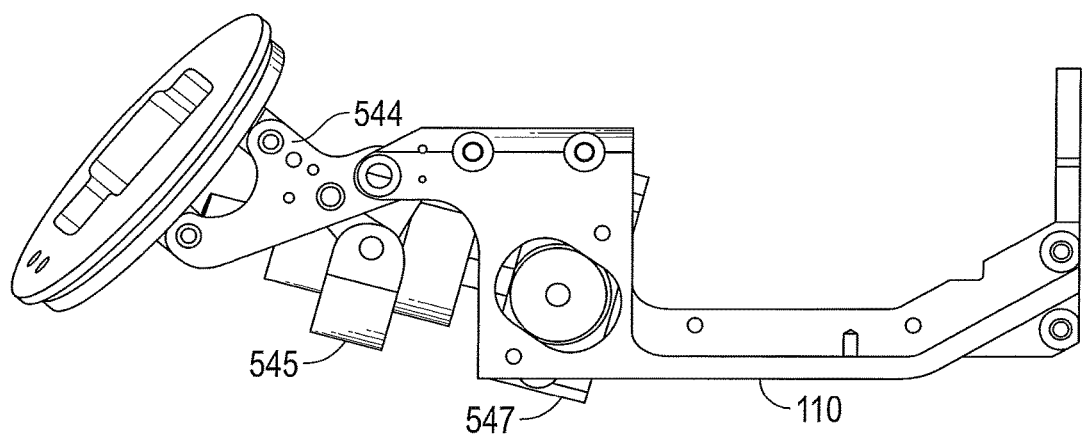
FIG. 20 shows a side view of the elbow of the prosthetic limb, according to one embodiment.

In an embodiment, the elbow 50 further comprises the elbow linkage 590 shown at FIGS. 19 and 20. In one embodiment, the elbow linkage 590 comprises the frame 110, the differential roller screw 540, a humeral frame 544, the roller screw nut 546, the thrust housing 547, a first nut link 548 and a second nut link 549. However, it should be understood that different link configurations could be used to assemble the elbow linkage 590. The elbow linkage 590 converts the linear motion of the differential roller screw 540 to rotary motion about the axis of rotation 560 of the elbow 50, via force applied thorough the roller screw bracket 545 and the roller screw nut 546. A user will typically use the limb 10 while in an upright position. As a result, the torque generated by gravitational forces is minimal when the elbow 50 is fully extended, as shown in FIG. 17, and is maximal when the elbow 50 is flexed 90 degrees. For this reason, the elbow linkage 590 has a kinematically defined non-constant gear ratio. The lengths of the four bars in the elbow linkage 590 may be optimized to minimize the linkage forces and the torque required to lift a constant weight from 0 to 135 degree range of motion of the elbow 50. The axis of the elbow linkage 590 is placed non-prisimatically relative to socket connector 95, such that elbow 50 has a natural carrying angle that mimics the carrying angle in humans. FIG. 19 shows the socket connector 95 at such an angle. As shown in FIG. 19, this carrying angle creates medial humeral rotation when the elbow 50 is flexed, allowing the hand 30 to reach the midline of the body without the need for a separate humeral-rotator. Two shear pins (not shown) connecting the elbow linkage 590 break when the elbow 50 is subjected to excessive torque, to prevent potential damage to the differential roller screw 540. Excessive torque might result if a user falls on the limb 10 or from an external force applied to the limb 10. The placing of shear pins allows for the arm to fail gracefully when needed. The shear pins may easily be replaced by a clinician or service technician, allowing for relatively inexpensive repair.

FIG. 17 shows elbow 50 in a position of relative extension and FIG. 18 shows the elbow 50 in a position of relative flexion. As shown in FIGS. 15-20, in one embodiment, the elbow may comprise a first limb portion, which may comprise the humeral frame 544, and a second limb portion, which may comprise the frame 110, coupled together at the elbow joint 551. A first end of the screw 540 is coupled to the first limb portion, for instance by threading the first end of the screw 540 through the roller screw nut 546, which is attached to the roller screw bracket 545 by the screws 552. The transmission housing 550 is coupled to the humeral frame 544 at a transmission joint, which in one embodiment is the hinge joint 130. When the screw 540 extends linearly in a direction away from the transmission housing 550, the screw 540 applies a force on the roller screw bracket 545 via the roller screw nut 546, which causes the humeral frame 544 to rotate about the elbow joint 551 towards the humeral frame 544. The rotation of the first limb portion towards the second limb portion is also known as the flexion of the elbow. When the screw 540 retracts linearly in a direction towards the transmission housing 550, the screw 540 applies a force on the roller screw bracket 545 that causes the humeral frame 544 to rotate about the elbow joint 551 away from the frame 110. The rotation of the first limb portion away from the second limb portion is also known as the extension of the elbow. In one embodiment, as the screw 540 extends linearly in a direction away from the transmission housing 550, the transmission housing 550 rotates about the hinge joint 130 in a first direction. As shown in FIG. 18 in comparison to FIG. 17, the transmission housing 550 rotates about the hinge joint 130 in a clockwise direction indicated by arrow 561. When the screw 540 retracts linearly in a direction towards the transmission housing 550, the transmission housing 550 rotates about the hinge joint 130 in a second direction opposite to the first direction. As shown in FIG. 17 in comparison to FIG. 18, the transmission housing 550 rotates about the hinge joint in a counter-clockwise direction indicated by arrow 562.

In some of the embodiments described herein, the limb 10 conforms to the body size of a 25th percentile adult female (17.8 cm/7" hand circumference) and has a sufficiently small mass in order to be most suitable for smaller users, such as women or children. It should be understood that the design of the limb 10 and its associated components can be scaled to accommodate other sized users. The components of the limb 10 described herein may be used with other prostheses components. For instance, the hand 30, the wrist rotator 90, and the wrist flexor 70 may be coupled to a prosthetic forearm of another manufacturer.

Each papers and articles noted herein are hereby incorporated by reference and available for inspection in the records of the United States Patent and Trademark Office for this patent.

In view of the many possible embodiments to which the principles of the present discussion may be applied, it should be recognized that the embodiments described herein with respect to the drawing figures are meant to be illustrative only and should not be taken as limiting the scope of the claims. Therefore, the techniques as described herein contemplate all such embodiments as may come within the scope of the following claims and equivalents thereof.

What is claimed:

1. A component part of a wrist of a prosthetic limb, comprising an exterior-rotor motor comprising a rotor and a stator; a planetary gear transmission comprising a plurality of planetary gears and a sun gear, the sun gear being fastened to the stator and engaged with the plurality of planetary gears; a clutch; and a cycloid transmission; in a transmission arrangement such that actuation of the exterior-rotor motor causes movement through the planetary gear transmission, clutch, and cycloid transmission to cause rotation of the wrist; wherein the rotor is positioned on the outside of the stator.

2. The wrist component of claim 1, wherein the exterior-rotor motor, a planetary gear transmission, a clutch, and a cycloid transmission are in a transmission arrangement such that actuation of the exterior-rotor motor causes movement through the planetary gear transmission, clutch, and cycloid transmission to cause movement of the wrist.

3. The wrist component of claim 2, wherein the clutch comprises a non-backdrivable mechanism for preventing output motion of the clutch to be transmitted to the cycloid transmission.

4. The wrist component of claim 3, wherein the planetary gear transmission is a single-stage planetary gear transmission.

5. The wrist component of claim 4, wherein the movement of the wrist is a rotational movement.

6. The wrist of claim 5, wherein the torque ratio of the planetary gear transmission is about 3.71:1 and the torque ratio of the cycloid transmission is about 16:1.

7. The wrist component of claim 4, wherein the movement of the wrist is a flexion movement.

8. The wrist component of claim 1, wherein an axis of rotation of the wrist component is skewed at a fixed position to provide radial or ulnar deviation.

9. A prosthetic limb comprising the wrist component of claim 1, the prosthetic limb further comprising an elbow, the elbow comprising:
   an exterior-rotor motor;
   a transmission comprising a planetary gear transmission, a non-backdrivable clutch, and a screw;

the screw adapted to receive a rotational force in a first direction from the clutch, and in response to the rotational force in the first direction, extend linearly with respect to the transmission so as to cause the elbow to flex.

10. A prosthetic limb comprising the wrist component of claim 1, the prosthetic limb further comprising:
a first limb portion and a second limb portion coupled together at an elbow joint;
a transmission comprising a screw, wherein a first end of the screw is coupled to the first limb portion at a bracket and the transmission is coupled to the second limb portion at a transmission joint;
wherein the screw and the hinge are adapted so that:
when the screw extends linearly in a direction away from the transmission, the screw applies a force on the bracket that causes the first limb portion to rotate about the elbow joint towards the second limb portion; and
when the screw retracts linearly in a direction towards the transmission, the screw applies a force on the bracket that causes the first limb portion to rotate about the elbow joint away from the second limb portion.

11. A wrist of a prosthetic limb, comprising:
a wrist rotator comprising a first exterior-rotor motor comprising a first stator; a first planetary gear transmission comprising a first plurality of planetary gears and a first sun gear, the first sun gear being fastened to the first stator and engaged with the first plurality of planetary gears; a first clutch and a first cycloid transmission, in a transmission arrangement such that actuation of the first exterior-rotor motor causes movement through the first planetary gear transmission, first clutch, and first cycloid transmission to cause rotation of the wrist;
a wrist flexor comprising a second exterior-rotor motor comprising a second stator; a second planetary gear transmission comprising a second plurality of planetary gears and a second sun gear, the second sun gear being fastened to the second stator and engaged with the second plurality of planetary gears; a second clutch; and a second cycloid transmission, in a transmission arrangement such that actuation of the second exterior-rotor motor causes movement through the second planetary gear transmission, second clutch, and second cycloid transmission to cause flexion of the wrist;
the first clutch comprising a non-backdrivable mechanism for preventing output motion of the first clutch to be transmitted to the first cycloid transmission; and
the second clutch comprising a non-backdrivable mechanism for preventing output motion of the second clutch to be transmitted to the second cycloid transmission;
wherein each of the first exterior-rotor motor and the second exterior-rotor motor further comprises a rotor, the rotor of each motor being positioned on the outside of the stator of the motor.

12. The wrist of claim 11, wherein at least one of the first planetary gear transmission and the second planetary gear transmission is a single-stage planetary gear transmission.

13. The wrist of claim 11, wherein the torque ratio of the first planetary gear transmission is about 3.71:1 and the torque ratio of the first cycloid transmission is about 16:1.

14. The wrist of claim 11, further comprising an interface on the wrist rotator for transmitting signals across an access of rotation of the wrist rotator.

15. The wrist of claim 14, wherein the interface comprises an interface for power signals and an interface for ground signals.

16. The wrist of claim 15, wherein the interface further comprises an interface for at least two communication signals.

17. A prosthetic limb comprising the wrist component of claim 14, the prosthetic limb further comprising an elbow, the elbow comprising:
an exterior-rotor motor;
a transmission comprising a planetary gear transmission, a non-backdrivable clutch, and a screw;
the screw adapted to receive a rotational force in a first direction from the clutch, and in response to the rotational force in the first direction, extend linearly with respect to the transmission so as to cause the elbow to flex.

18. A prosthetic limb comprising the wrist component of claim 14, the prosthetic limb further comprising:
a first limb portion and a second limb portion coupled together at an elbow joint;
a transmission comprising a screw, wherein a first end of the screw is coupled to the first limb portion at a bracket and the transmission is coupled to the second limb portion at a transmission joint;
wherein the screw and the hinge are adapted so that:
when the screw extends linearly in a direction away from the transmission, the screw applies a force on the bracket that causes the first limb portion to rotate about the elbow joint towards the second limb portion; and
when the screw retracts linearly in a direction towards the transmission, the screw applies a force on the bracket that causes the first limb portion to rotate about the elbow joint away from the second limb portion.

19. The wrist of claim 11, further comprising a mechanical stop to limit motion of the wrist flexor.

20. The wrist of claim 11, wherein the wrist rotator and the wrist flexor are connected by a coupler that allows for the transmission of power from the wrist rotator to the wrist flexor.

21. The wrist of claim 11, wherein an axis of rotation of the wrist flexor is skewed at a fixed position to provide radial or ulnar deviation.

22. The wrist of claim 11, wherein the non-backdrivable mechanism comprises a plurality of rollers and a plurality of springs.

23. A prosthetic limb comprising the wrist component of claim 11, the prosthetic limb further comprising an elbow, the elbow comprising:
an exterior-rotor motor;
a transmission comprising a planetary gear transmission, a non-backdrivable clutch, and a screw;
the screw adapted to receive a rotational force in a first direction from the clutch, and in response to the rotational force in the first direction, extend linearly with respect to the transmission so as to cause the elbow to flex.

24. A prosthetic limb comprising the wrist component of claim 11, the prosthetic limb further comprising:
a first limb portion and a second limb portion coupled together at an elbow joint;
a transmission comprising a screw, wherein a first end of the screw is coupled to the first limb portion at a bracket and the transmission is coupled to the second limb portion at a transmission joint;

wherein the screw and the hinge are adapted so that:
when the screw extends linearly in a direction away from the transmission, the screw applies a force on the bracket that causes the first limb portion to rotate about the elbow joint towards the second limb portion; and when the screw retracts linearly in a direction towards the transmission, the screw applies a force on the bracket that causes the first limb portion to rotate about the elbow joint away from the second limb portion.

\* \* \* \* \*